United States Patent
Harnsberger et al.

(10) Patent No.: US 7,593,967 B2
(45) Date of Patent: Sep. 22, 2009

(54) ELECTRONIC CLINICAL REFERENCE AND EDUCATION SYSTEM AND METHOD OF USE

(75) Inventors: Hugh Harnsberger, Salt Lake City, UT (US); Anne Osborn, Salt Lake City, UT (US)

(73) Assignee: Amirsys, Inc., Salt Lake City, UT (US)

( * ) Notice: Subject to any disclaimer, the term of this patent is extended or adjusted under 35 U.S.C. 154(b) by 319 days.

(21) Appl. No.: 10/723,018

(22) Filed: Nov. 26, 2003

(65) Prior Publication Data
US 2004/0107118 A1    Jun. 3, 2004

Related U.S. Application Data

(60) Provisional application No. 60/429,933, filed on Nov. 27, 2002.

(51) Int. Cl.
G06F 17/30 (2006.01)

(52) U.S. Cl. ........................ 707/200; 707/101

(58) Field of Classification Search .............. 707/1–6, 707/10, 100–102, 200; 705/2
See application file for complete search history.

(56) References Cited

U.S. PATENT DOCUMENTS

| 6,076,091 | A | 6/2000 | Fohn et al. |
| 6,263,330 | B1* | 7/2001 | Bessette ........................ 707/4 |
| 6,551,107 | B1 | 4/2003 | Buckley et al. |
| 6,757,898 | B1* | 6/2004 | Ilsen et al. ................... 709/203 |
| 6,850,944 | B1* | 2/2005 | MacCall et al. ............. 707/100 |
| 2002/0069215 | A1* | 6/2002 | Orbanes et al. ............. 707/200 |
| 2003/0013951 | A1* | 1/2003 | Stefanescu et al. .......... 600/407 |

OTHER PUBLICATIONS

U.S. Appl. No. 10/516,554, filed Mar. 23, 2006, Patricia Goede.

* cited by examiner

Primary Examiner—Mohammad Ali
Assistant Examiner—Marc R Filipczyk
(74) Attorney, Agent, or Firm—Workman Nydegger

(57) ABSTRACT

A clinical reference and education system and method of use, wherein medical condition diagnosis information is gathered, stored, and distributed. More specifically, information regarding clinical/pathological differential analyses, key facts, clinical presentations, pathology features, imaging findings, anatomy information, medical references with abstracts, expert imaging center information, continuing medical education information, and related data is made available in electronic and printed forms via a general infrastructure of the present system.

18 Claims, 21 Drawing Sheets

FIGURE 9

ELECTRONIC CLINICAL REFERENCE AND EDUCATION SYSTEM AND METHOD OF USE

PRIORITY INFORMATION

This application claims the priority date of U.S. Provisional Patent Application No. 60/429,933, filed Nov. 27, 2003.

BACKGROUND OF THE INVENTION

It is well known in many fields of knowledge or professions, such as the medical profession, to use reference books and other printed publications to assist practitioners in conducting their required duties. For example, doctors often consult medical references when diagnosing patients. These medical reference materials typically provide a variety of information, such as the names of established diagnoses, radiological images and/or medical illustrations, imaging findings, differential diagnoses, typical pathologies, common clinical issues, and a host of other helpful materials/content. For hundreds of years, hardbound reference books have been the dominant source of medical information. However, with the advent of electronic data storage and transfer techniques, electronic libraries are becoming widely utilized.

More particularly, the recent introduction of the Internet and the world wide web ("WWW") to the world of communication and media has increased the general ability to disperse and disseminate reference materials and related information. Extensible markup language ("XML") was formed under the auspices of the World Wide Web Consortium ("W3C®"), an international consortium of companies involved with the Internet and the WWW. XML is a flexible, and relatively simple, text format that was originally designed specifically for electronic publishing. XML has become a widely utilized medium for the exchange of data on the WWW. Some examples of the implementations of XML, as particularly related to the dissemination of medical reference materials, are outlined generally below.

Using the WWW as an example of an immense heterogeneous database, it makes sense that utilization of XML benefits for describing data could be adapted on a smaller scale to an environmentally closed system. In fact, the broad benefits of XML markup have been recognized for improving efficacy of databases, and traditional database vendors (such as Oracle®, IBM®, and Microsoft®) have fast-tracked XML implementation modules for their traditional databases and have (or are) designing XML native DB's. Already, a cottage industry has arisen for XML-native databases that do not require the construction/deconstruction events of the traditional database programs.

This language allows designers to create their own customized tag elements, enabling the definition, transmission, validation, and interpretation of data between applications, and has been a boon to the business community, particularly publishers. It has had a profound impact on a variety of applications ranging from inter-bank transactions, to online catalog maintenance, to updating and modification of customer service records. For the first time, XML has enabled efficient description of heterogeneous data sources allowing for computer-to-computer exchange between often-discordant database environments.

In relation to the publishing of reference materials, such as medical texts or treatises, XML has been utilized as the supporting language to a variety of sources, including: UMLS® Metathesaurus®, SPECIALIST Lexicon, and UMLS® Semantic Network.

UMLS® Metathesaurus® (the "Metathesaurus®") currently contains content from over 60 biomedical vocabularies and classifications. It preserves the names, meanings, hierarchical contexts, attributes, and inter-term relationships present in its source vocabularies, adds certain basic information to each concept, and establishes new relationships between terms from different source vocabularies. The Metathesaurus® supplies information that computer programs can use to interpret user inquiries, interact with users to refine their questions, identify which databases contain information relevant to particular inquiries, and convert the users' terms into the vocabulary used by relevant information sources. The Metathesaurus® is intended primarily for use by system developers, but can also be a useful reference tool for database builders, librarians, and other information professionals.

UMLS® SPECIALIST Lexicon (the "SPECIALIST") is a general English lexicon intended for use by natural language processing systems. Each lexicon entry for each word or term records the syntactic, morphological, and orthographic information needed by the SPECIALIST natural language processing system. The lexical programs generate a range of variations for English lexical items, which should be useful for recognizing lexical variation in biomedical terminologies and texts, and consist of several different modules that may be combined in a variety of ways. Several lexical databases that may be useful for developers are available and include a file of known derivational variants, a file of closely related terms that mean the same thing but may have a different syntactic category, a file of spelling alternations, and a file of neoclassical combining forms with their meanings.

UMLS® Semantic Network (the "Semantic Network") provides 134 semantic subtypes to provide consistent categorization of all concepts within the Metathesaurus® with 54 links between semantic subtypes. While all information about specific concepts is found in the Metathesaurus®, the Semantic Network provides information about the basic semantic types that are assigned to these concepts, and it defines the relationships that hold between the semantic types. Thus, the Semantic Network serves as an authority for the semantic types that are assigned to concepts in the Metathesaurus®. It defines these types, both with textual descriptions and by means of the information inherent in its hierarchies.

System developers can use these UMLS® products free of charge after applying for a UMLS® license. Applications of UMLS® can be found in systems focused on patient data, digital libraries, Web and bibliographic retrieval, natural language processing, and decision support.

MeSH, yet another known lexical product, provides a simple layer in that it consists of a thesaurus with a set of terms or subject headings that are arranged in both an alphabetic and a hierarchical structure. It contains more than 19,000 main headings as well as 103,500 headings called Supplementary Concept Records within a separate chemical thesaurus. There are also thousands of cross-references that assist in finding the most appropriate MeSH heading (e.g., Vitamin C see Ascorbic Acid). MeSH is free to users and an electronic form can easily be downloaded.

Most of the existing work on developing the "semantic web" has focused on finding ways to express relationships between existing resources (i.e., content). This has led to the development of the Resource Description Framework ("RDF") and the RDF Schema ("RDFS") as forms for expressing relationships and semantic metadata. RDF is a general framework used for describing metadata and provides interoperability between applications that exchange machine-understandable information. RDFS is a specification that describes how to use RDF to describe RDF vocabularies and defines a basic vocabulary for this purpose, as well as conventions that can be used by semantic applications to support a more sophisticated RDF vocabulary description. A further development has been the DARPA Agent Markup Language ("DAML") and the Ontology Inference Layer ("OIL") specifications, which are currently being combined to produce DAML+OIL. DAML+OIL is a semantic markup language for Web resources that builds upon the earlier W3C® standards of RDF and RDFS, extending these languages with richer modeling primitives allowing more complex objects and operations to be constructed.

Despite the reference products that are currently available, as generally outlined above, there still exists some unique and challenging problems with the current state of the art, as outlined below.

Problems with the Prior Art

It is recognized that the following problems have existed, and do exist, in the prior art with respect to the availability, relevance, and form of medical reference information: a general lack of logistical ease of production and use of reference materials; a lack of an ability to produce readily usable content in a timely manner; a lack of an ability to repurpose author-generated content data; a lack of an ability to use author-generated content; and a lack of an ability to extract lexical information from a topic map and link this lexical layer to existing standard controlled vocabularies and thesauri (as are outlined above).

With respect to the lack of logistical ease of production and use of reference materials, both conventional and modern uses of hard copy libraries and hand-carried electronics devices, such as PDA devices, respectively have inherent disadvantages for medical practitioners. Typically, hard copy reference materials are located within a central library and/or specially designated reading areas of a hospital or other facility, which is often inconvenient to visit and access at the time of a needed diagnosis. Hard copy materials (e.g., books and medical journals) at these centralized locations are often out-of-date or not available when needed for immediate reference. Similarly, personal electronic hand-carried devices, while more convenient, have significant limitations as to the volume of content which can be held therein, limited small size of graphical image display, as well as the processing speed and complexity of data.

In addition, medical reference materials, whether in hard copy, hand-held personal reference or traditional electronic form, are written in the author's prose, and organized idiosyncratically with each individual author's format and wording. The constant inconsistency of format, wording, and organization greatly impedes a physician's ability to navigate texts or databases in the effort to find the relevant and appropriate information.

Medical reference materials are also inherently difficult to share. In hard copy form, physicians are forced to either copy the relevant text from a library source (often ignoring copyright laws and subjecting themselves to possible illegal activity) or to cut and paste relevant excerpts from electronic databases on a network or Internet website. These challenges ultimately serve as deterrents to quickly and easily sharing valuable information between sources and/or physicians. Such deterrents may impede a physician's ability to provide optimal patient care.

With respect to the lack of the prior art to produce readily usable content in a timely manner, it often takes years to complete the process of publication from an initial thought, which leads to out-of-date reference content on the very day of publication. In addition, the many hours wasted with the multiple manual processes inherent to text and image management are frustrating to authors to the point that they consider never writing another textbook. Authors, especially in the area of medicine, need a new and improved system to better and more timely communicate critical, new life-saving information to the medical community in the effort to better serve patients.

Currently, authors must rely heavily on time-intensive hand entered manipulations of medical images and text. Typically an author has about two years to submit final content, at which time the publisher must organize the data into a print acceptable format for production. Publications are then distributed by a sales and distribution labor force. This usually takes a minimum of two to four years, from initial author contract to product availability. This is part of the reason why textbooks are historically referred to as "tertiary" forms of information, usually containing out-dated information at the time of publication. This time frame must be shortened in order to increase the relevance and impact of the information, in turn impacting the accessibility of learning materials with direct implications on patient care and resultant healthcare expenditures.

Information in both hard copy and electronic form is continually lagging behind the pace of technological innovation and the accumulation of medical knowledge. Presently, there is no easy way for end users to augment third-party reference materials with updated or ground breaking information and to transmit it to members of the profession, or to simply create a fast and integrated record of personal notes, observations, or discoveries as an addition to established reference materials. Arguably, this lack of such augmented medical information could potentially create instances of medical liability for doctors that fail to access an active, and up to date, medical reference library.

Now referring to the current inability to repurpose author-generated content data, moving documents into and out of an extensible markup language ("XML") relational database involves document composition and decomposition, which is handled by stored procedures. In order to transfer data between XML documents and a database, it is necessary to map the XML document schema to the database schema, and the data transfer software is then built on top of this mapping. The software may use an XML query language, such as W3C® XPath, or simply transfer data according to the mapping. XPath uses a sophisticated set of rules or syntax used for identifying specific pieces of an XML document. One can specify particular elements or attributes and their content, as well as individual pieces of content, or strings, based on the elements around them. However, XPath expressions by themselves are not much good, and to be of use, must be combined with other applications.

With respect to the inability to use author-generated content, there are difficulties recognized within the prior art in creating a semantically aware topic map with marked up tool support. Although XML has enabled efficient handling of heterogeneous data markup by describing content contained within tags rather than format, which has been termed "metadata" or "data about data", there is a clear lack of definitional or existential relationships between concepts. In fact, major efforts are well underway for developing tools to create relationships, or "ontologies", in this manner. This includes work at the Knowledge Sharing Laboratory at Stanford University, The High Performance Knowledge Base Initiative sponsored by the US Defense Advanced Research Projects Agency (DARPA) and at the University of Maryland by James Hendler, who also co-Chairs the W3C® Working Group on Semantic Activity. In addition, commercial products are becoming available for purchase, such as that from Applied Semantics®. However, commercial products are narrowly aimed at business applications for streamlining more efficient business and financial transactions in a business-to-customer or business-to-business environment.

Finally, the prior art has the inability to extract lexical information from a topic map and link this lexical layer to existing standard controlled vocabularies and thesauri. A "lexicon" is defined as "a stock of terms used in a particular profession, subject, or style," and a medical lexicon thus refers to an agreed upon nomenclature for medical communications standardization. For example, a multi-institutional study evaluating radiology nomenclature used within it documented 14 different ways of saying "interstitial edema/infiltrate" and 23 ways of suggesting the presence of an abnormality. Clearly adoption of a medical lexicon is needed by the medical community to allow physicians to communicate using a common vocabulary to ensure clarity of meaning, consistency in aggregation and ease of messaging. Without a standard "clinical terminology" that can be programmed into software to help computers understand what doctors are saying, it will be tougher to make the shift to widespread adoption of electronic medical records. Ultimately, adoption of a medical lexicon by the medical community will improve patient care, reduce errors inherent in data coding, facilitate of research, and support compatibility across software applications.

While semantic and ontology research is in its infancy, the underpinnings of broad-based application to large heterogeneous datasets is believed to be in place and to be backed by the highly-respected steering organization W3C® as well as very well funded entities such as DARPA. Accordingly, expectations of academicians are high for technical success. Commercial semantic products are already becoming available, yet they are designed for use in the business transactions environment only. Thus adaptation of a semantic structure, which is only made possible by the invention's XML enabled topic map driven approach within the publishing content database, is highly innovative and will further facilitate publishing, data repurposing and access by end-user physicians to facilitate accurate, faster digital diagnostic decision support.

All of the above proffered medical reference materials issues may lead one skilled in the art of medical diagnosis to conclude that the current system and method of gathering, storing, and distributing valuable medical information and knowledge is inefficient and problematic.

SUMMARY OF THE INVENTION

The present disclosure teaches one skilled in the art a unique system and method of gathering, storing, and distributing valuable information and knowledge. More specifically, the present system and method allows for easy access to reference information regarding diagnoses and medical education, such as: terminology, clinical/pathological differential diagnosis details with links to specific diagnosis information; custom differential diagnoses and diagnostic checklist capturing "pearls of diagnostic wisdom" from leading experts; key facts; clinical presentation; pathology features; imaging findings; related images, such as clinical, gross pathology and histopathology photos and drawings; related anatomy information; references with abstracts; links to case information, such as index cases, common cases and uncommon/variant cases; case information; expert imaging center information, such as providing critical protocols, validate procedures and research guidelines; continuing medical education ("CME"); web service which will use the device's API to export data for other uses; content management, both for content submission and content approval; systems management for system usage and tracing analysis; branding/licensing management and system administration; and a host of other important related materials. There is also disclosed a unique system and method for allowing one skilled in the appropriate art to create medical annotations and attach these annotations about any diagnosis provided in the library to medical images.

Generally, the invention utilizes a unique system of comprehensive template applications to autoload medical data into a database. This allows the direct export of data that can be used for the creation of medical reference books and PDA-books semi-automatically. The data can also be directly exported to a digital diagnostic reference system that can assist a physician-user to search the data and to reach an accurate differential diagnosis more rapidly than using reference books. The invention will result in an XML enabled database that has been populated with author content created from the outset by XML metadata incorporating tools obviating any need for conversion of legacy data. This content is well formed XML, adhering to an underlying, and tool enforced, expanded outline. A semantic database layer facilitates data exchange with improved computer to computer and human to computer interactions. A lexical database layer supports improved data interchange, with a Metathesaurus® effect. A database style routine layer on the backend will make possible data repurposing events for innovative product creation.

Each step alone is believed to be innovative and not to have been adopted by the publishing industry or medical reference industry, yet is perceived to be the future of media-independent publishing by redefining the life cycle of a publication. In particular, there is provided a digital medical reference library containing over a thousand diagnoses on a PC, a server for online access, a picture archives and communication system ("PACS") device, radiological information system ("RIS"), electronic medical records ("EMR"), or other similar storage and processing devices.

The invention enables a user to modernize traditional, antiquated medical publishing and medical reference methods, and, by so doing, facilitate the production of content in a much more timely manner. The ability to take well-formed author content and repurpose it into varying formats, depending on demand of the end-user, with a minimum amount of human interaction is considered to be novel and will enable the invention to make available learning materials in a more expeditious manner that are more up-to-date at the time of publication and/or distribution. Currently, it is recognized that this process of publication production and medical reference is not being used.

As a result, the present system and method may yield unprecedented capabilities for knowledge extraction and presentation, and at the very least the ability to repurpose content to produce new printed, electronic or other digital products. Further, extending that power into user-customized texts is not significantly more complex, and the invention will be able to customize content based on context, such as the content the user is currently, or most recently, viewing is used to locate and suggest "what's related" topics.

Another feature of the present system and method, termed extensible stylesheet language formatting objects ("XSL-FO"), is in essence a content formatting library that will provide for translation of XML documents into formats needed for display devices of all types, from printers to web browsers to PDA's to digital diagnostic reference systems. There has yet to be universal adoption of an XSL-FO standard, and software support has been limited. The current recommendation can already be adopted for PDF output and output to a digital diagnostic reference system. It is expected that this form of technology will then evolve into a standard of its own.

While XML databases exist, their application to publishing and digital reference, let alone medical publishing and medical reference, is incomplete at best. By way of example, some companies in the publishing industry apply XML technology to their professional journals. Specifically, they convert their existing journal content into an XML format that is used to sell journals in an electronic format on the WWW. Separately, they also utilize XML in their business end for tracking orders as well as handling their catalogs. The present invention's use of XML enabled processes at all levels of content manipulation, from author content acquisition to final production, is innovative and a novel application of what is already cutting-edge technology.

Now referring to the semantic properties and capabilities of the present system and method, integrating semantic technologies into the database will also allow for several innovative features, heretofore unavailable, allowing the invention to: intelligently constrain search terms based on semantic relationships leveraging what the system "knows" about disjoint sets to reduce the cognitive load on the human searcher; incorporate explicit and inferred information about preferences and areas of interest, ultimately reducing the cognitive effort required for navigation; explore the human-interface aspects of navigating information space, particularly the transition between querying and browsing; improve natural-language search capability by leveraging ontological information; prove consistency of the ontology; and merge internal and external resources.

To further the invention, certain Java-based desktop tools are created to support this type of application-aware content creation. The first tool is a master outline authoring tool ("MOAT") that enables certain authors to define multiple parallel logical links between each diagnosis name in a set of diagnosis names, such as all the diagnoses in the table of contents of a diagnosis reference book, and multiple organizational hierarchies, such as anatomy and pathology hierarchies. Behind the scenes, MOAT captures and stores these links in XML, which is then loaded into an XML database. The second tool is a case authoring tool ("CAT") that enables each author to select, order, and name each of the multiple radiology or other images that belong to a case, where each case is associated with a specific imaging study for a specific (but anonymous) patient. CAT allows an author to enter text case descriptions, links to pertinent diagnostic names, case types, generic patient demographics, generic case histories, and other related information. Behind the scenes, MOAT captures and stores each case in XML with its images, which data are then loaded into an XML database. The third tool is a diagnosis authoring tool ("DAT") that can be used by each author for generation of diagnosis text content and selection of relevant images from cases, with a simple and easy to use graphical user interface ("GUI") that is Windows-based and provides constrained editing fields that guide the author in structuring the content. DAT allows an author to enter text content compatible with digital database information, including diagnosis information, key facts, imaging findings, etc. These tools apply commonly used processes for handling XML data. Behind the scenes, the DAT authoring tool places the written content within predefined XML tags that identify the purpose and meaning of each content portion.

One of the current embodiments of CAT and DAT include an annotation tool that operates in similar fashion on image data by handling labels, titles, captions and legends as defined in an annotation definition. This annotation tool may apply vector-based annotations upon a raster image without permanently altering the image. This can be performed by utilizing an image format, such as portable network graphics ("PNG"), that can incorporate the annotations as well as accompanying metadata separately, yet within the same file as separate chunk data. Such images can then be easily viewed in interactive fashion, by allowing all, some, or none of the stored data to be viewed, depending on user choice, when read by software written incorporating scalable vector graphics ("SVG") language. SVG is an XML based vector graphics language, and already plug-ins are available for use in Microsoft Explorer (available from Microsoft, Corporation of Redmond, Wash.) and Netscape Communicator (available from Netscape Communications Corporation, based in Mountain View, Calif.).

Given the invention's radiological origins, the first tool versions were designed to bring radiology educational and reference products into production as quickly as possible.

With these XML tools in place, an XML enabled database may be populated with author content as quickly as it is received. It is noted that under the invention, it is not necessary to convert legacy data into XML, as the invention's content will already have been created in an XML environment from the outset. This will then allow the invention to build XML processes upon this foundation. However, it is noted that the data in an XML-tagged form only provides the substrate. The present invention also provides for the development of an ontology layer above the XML data. In one embodiment the ontology layer is a topic map.

Topic maps are a developing technology first described in ISO/IEC 13250:2000, and more recently extended into XML format in XTM specifications. The purpose of a topic map is to convey knowledge about resources through a superimposed layer, or map, of the resources. A topic map captures the subjects of which resources speak, and the relationships between subjects, in a way that is implementation-independent. One of the particular strengths of the topic map paradigm is the ease with which terms can be linked and cross-referenced.

A crucial difference between W3C® standards, such as DAML+OIL and topic maps is the underlying philosophy. While DAML+OIL and the lower layers of RDF/RDFS express relationships between existing resources, topic maps express concepts and relationships independently, with resources and data then tied to the ontological worldview. This approach has significant advantages in the invention's application, and one of the key tasks of this goal is to encode the expert knowledge of certain luminary authors into a master topic map that serves as a navigation space for the XML-tagged content. One of the particular advantages that topic maps offer is a carefully defined and specified processing model. This provides a significant level of interoperability between topic maps, with well-known merge semantics. It will also enable automatic transformation to and from RDF/RDFS formats, which will allow the invention's systems to ultimately interface with other RDF/RDFS-enabled systems.

The invention's integration of a medical lexicon will help bridge across heterogeneous terms that different authors may use. As all data is XML enabled in the invention's database, a lexical layer interacting with semantics at the level of ontologies and a thesaurus will further extend the invention's ability to repurpose data with a minimum of human intervention. The more tasks that can occur via a computer-to-computer interface decrease not only time involved in the path to a final product but also in overhead cost.

One advantageous feature of the present invention, from an implementation perspective, is that it can require a lexicon be set. Specifically, one embodiment of the present invention needs to produce integration of controlled vocabularies with dynamic, statistically inferred indexes. It can start from a relatively controlled vocabulary, based on its author tool enforced "Expanded Outline", which can be linked to the lexicon so that ultimately there will be more knowledge that can be extracted efficiently a posteriori.

The information outlined above is the current cutting edge of XML database implementations. The present invention seeks to extend this current knowledge even beyond this level. Because it has a significant amount of semantic content encoded in the topic map, the present invention has the ability to access and retrieve content in ways that are virtually impossible using XPath or XQuery. These methods utilize the structure of the XML documents to locate data. Expressions of XPath can be used to point software to a particular spot within a document, select a node, or series of nodes, that can either be transformed from an XML element set into another set or have styles applied to them via XSL-FO, or include XML query language for retrieving data from XML documents.

The semantic technologies of the present invention are able to use the relationships of the concepts themselves to locate data. XPath and XQuery require a human to understand what the "meaning" of the XML structure is and queries must be modified every time this structure changes. By contrast, the semantic relationships reflect "real" concepts and queries are independent of underlying structure.

Thus, the invention can combine semantic organization capabilities with XSL-FO to produce final products. XSL-FO is of particular interest to the invention, in that it defines how XML documents should be displayed or converted into various forms of output, such as Adobe Acrobat portable document format ("PDF").

By providing authors with an application-specific content entry tool, it is possible to include XML encoding at the time of content creation that marks specifically identified portions of the text, that may contain certain meaning for example. This allows the authors to retain creative freedom in writing the content while giving the systems that process the content "knowledge" about it—for example, the system can automatically keep track of words that the author has identified as synonyms.

The next step, now that certain knowledge is encoded in a computer-readable form, is to extract individual concepts and identify the relationships between them. This involves using human understanding to link certain core concepts, and then allowing the system to manage the application of these concepts across large quantities of data. The result of this process is an "ontology"—a formally expressed representation of a certain body of knowledge. The ontology will contain rules that express definitional or existential relationships between concepts, as well as inference rules that enable the system to infer relationships based on other explicitly stated rules.

Additional features and advantages of the invention will be set forth in the detailed description which follows, taken in conjunction with the accompanying drawings, which together illustrate by way of example, the features of the invention.

BRIEF DESCRIPTION OF THE FIGURES

FIG. 9 depicts a CAT Image Screen according to one embodiment of the present invention.

DETAILED DESCRIPTION OF THE ILLUSTRATED EMBODIMENT

Figure 1:
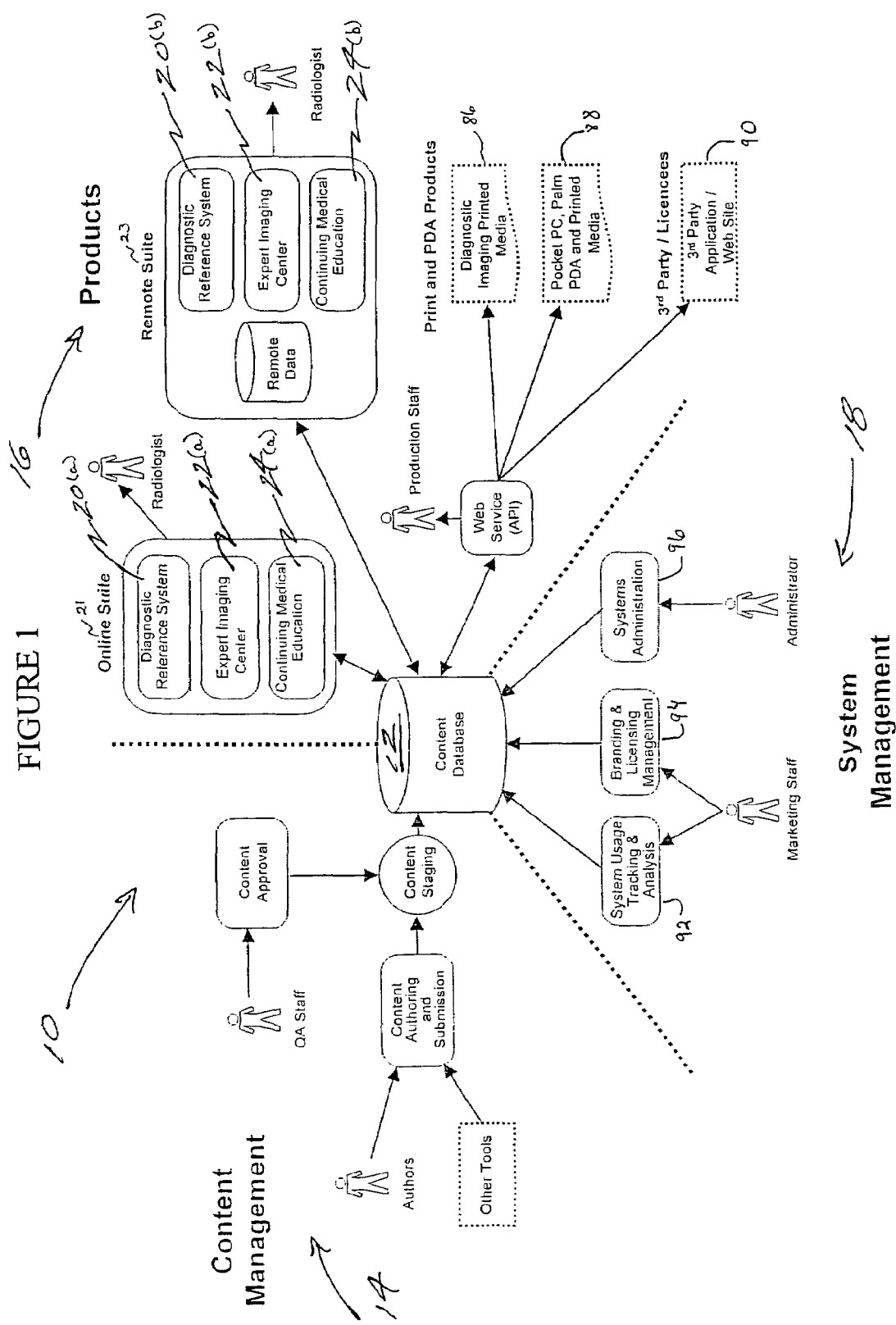
FIG. 1 depicts a System Flow Chart of one embodiment of the present invention illustrating an overview of how the present system and method allows full integration of information publishing and distribution to and through products.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

In an effort to solve the problems identified in the prior art, as outlined above, the present system and method is generally designed to intelligently constrain search terms based on semantic relationships leveraging what the system "knows" about disjoint sets to reduce the cognitive load on the human searcher, to incorporate explicit and inferred information about preferences and areas of interest, to reduce the cognitive effort required for navigation, to explore the human-interface aspects of navigating information space, to improve natural-language search capabilities by leveraging ontological knowledge, to prove consistency of the ontological knowledge, and to merge internal and external resources.

Now referring to FIG. 1, a flow chart illustrating a general overview of how the present system method provides for full integration of an information publishing process 10 with a content database 12 at the center surrounded by content management 14, product deployment 16, and system management 18 sub processes. The content management subprocess 14 provides integration of authors, tools, content authoring and submission, quality assurance, content approval and content staging. The products deployment subprocess 16 includes an online suite 21 of reference and education systems including a diagnostic reference system 20(a), an expert imaging center system 22(a), and a continuing medical education system 24(a) for distribution, for example only, to radiologists or other medical professionals. Further, the products deployment subprocess 16 includes a remote suite application 23 of the above-described products, (as with the online suite 21, the remote suite 23 similarly includes a diagnostic reference system 20(b), an expert imaging center system 22(b), and a continuing medical education system 24(b)) for distribution, for example only, to radiologists or other medical professionals. Further, the products deployment subprocess 16 includes a print and PDA products application that are related reference products, including diagnostic imaging print titles 86, other print and PDA titles 88, and third party licenses 90 for accessing content from the database for applications or web sites, for example. The system management subprocess 18 includes tools for system usage tracking and analysis 92, branding and licensing management 94, and systems administration 96. In one embodiment of the Invention, access to the content database 12 can be achieved through a system management 18 "console" that can include system usage tracking and analysis 92, branding and licensing management 94 and systems administration 96 tasks such as content maintenance, update and edit.

More specifically, the diagnostic reference system 20(a) is an on-line reference database with a search engine that provides direct and immediate access to high-quality authored content that is comprehensive in terms of number of cases, associated images, depth of write-up, and breadth of related differential diagnoses, treatment options, and prognostic implications. The diagnostic reference system 20(a) is not constrained by page count limitations and hence allows for unlimited numbers of classical cases plus unlimited numbers of unique or rare cases to be included in the diagnosis discussion. In addition, the on-line platform allows for dynamic video clips and interactive anatomical animations that simply are not possible in print. Semantics will allow for intelligent searches yielding relevant results, and the lexical layer will not only search for the user specified topic, but for topics linked via the ontological layer.

The expert imaging center system 22(a) may be used by radiologists and other medical professionals to plan an imaging study, look up protocols, validate procedures and research guidelines. It is a web based application for providing imaging professionals the required access to expert information needed to optimize their imaging studies. In addition, the "look and feel" of this functionality may be customizable for OEM licensing.

The continuing medical education system 24(a) may be divided into two distinct subcatoegories: disease specific learning material and custom learning material. For disease specific learning material, data for single diseases can be extracted. For example, it could easily produce a text for Von Hippel Lindau Syndrome ("VHL"), which would include a full breadth of content from primary care physician diagnosis to neuroradiology description of disease findings in the spine to neurosurgery approaches for tumor resection to anesthesia care of the VHL patient intraoperatively, etc. With the invention's ability to repurpose data into choices of format, it can provide this "text" in electronic form for either handheld or desktop computer. Such learning material has not been possible previously. This has been the case primarily because it has been nearly impossible to coordinate disease specific content authors from all medical specialties; whereas, the present invention maintains such content in its content database 12. Additionally, due to the small size of many of these sub-specialty markets, the print publication cost of such traditional textbooks could not be offset by the income derived from the low volume of print product sales. The present invention's multi-authored content, streamlined processes, and technically innovated database design enable it to repurpose content into such a variety of products in a cost-effective manner. In fact, output to electronic format would incur minimal post-production costs, and the product could be downloaded or emailed.

Alternatively, custom learning material utilizes a set of WWW pages wherein a physician can check boxes of subject matter of interest to him/her. Nested within each field may be sub-category choices as detailed and deep as the user chooses. At the conclusion of custom designing the product, the user may enter payment information and a choice of product format. Electronic learning materials can then be generated completely by computer-to-computer interactions without human intervention and be distributed electronically. In such a scenario, there would be little to no production cost. Only by implementing the technical advances in the invention can this capability become reality. The ability to order custom learning material that is comprehensive for a patient's specific disease process will raise the educational level of patients, thereby enabling them to make more informed decisions regarding their healthcare.

Figure 2:
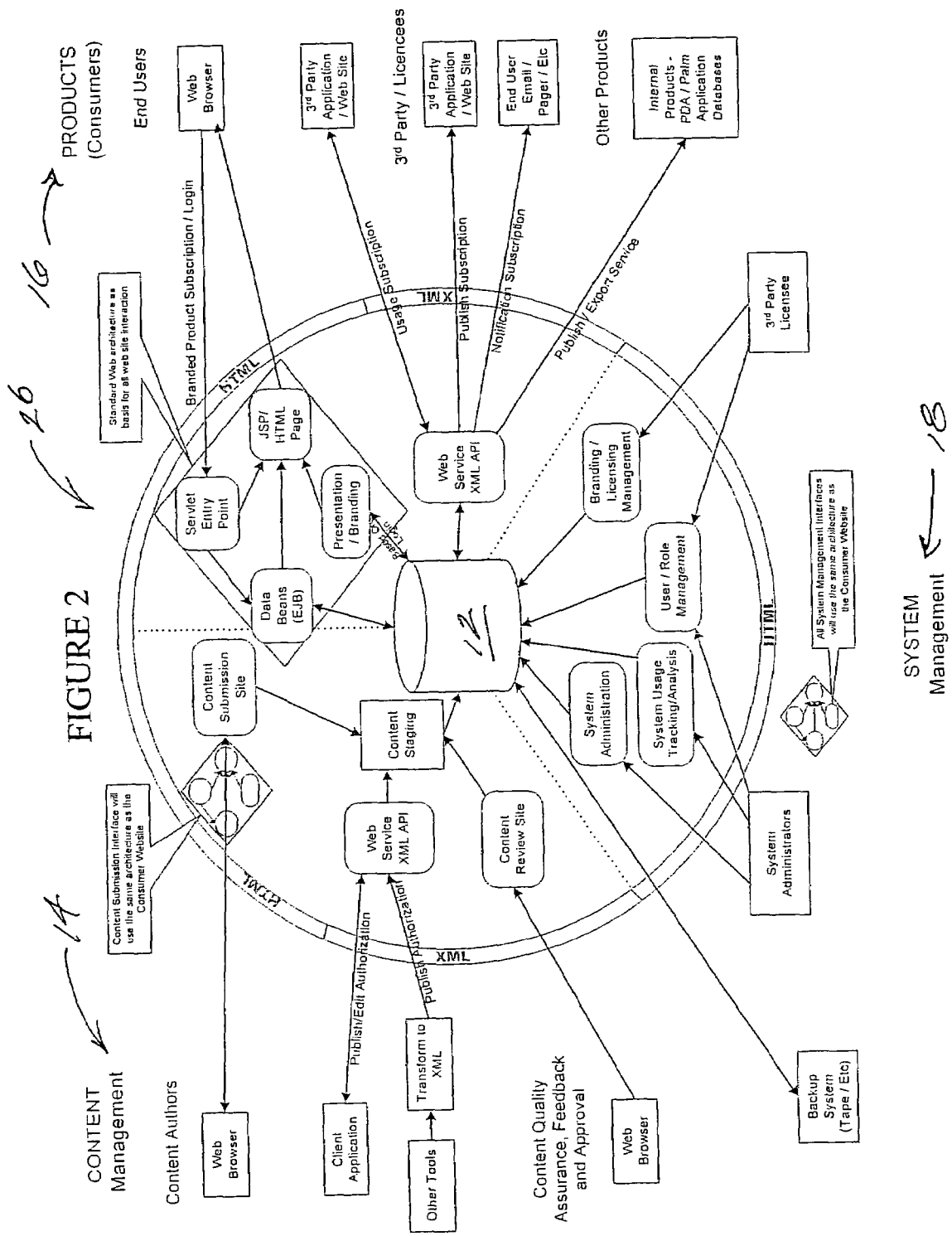
FIG. 2 depicts a High Level Infrastructure Chart illustrating a high level view of one embodiment of the present method and system's infrastructure, including content management, products and system management.

Referring now to FIG. 2, there is shown a chart illustrating a high level view of a general technical infrastructure 26 suitable for use with the present system and method. As described in FIG. 1, the general infrastructure 26 is divided into three areas: content management 14, product deployment 16 and system management 18. More specifically, FIG. 2 graphically describes the technical architecture and indicates the relationship between the utilization of HTML and XML in content management 14, products 16 and system management 18.

Figure 3:
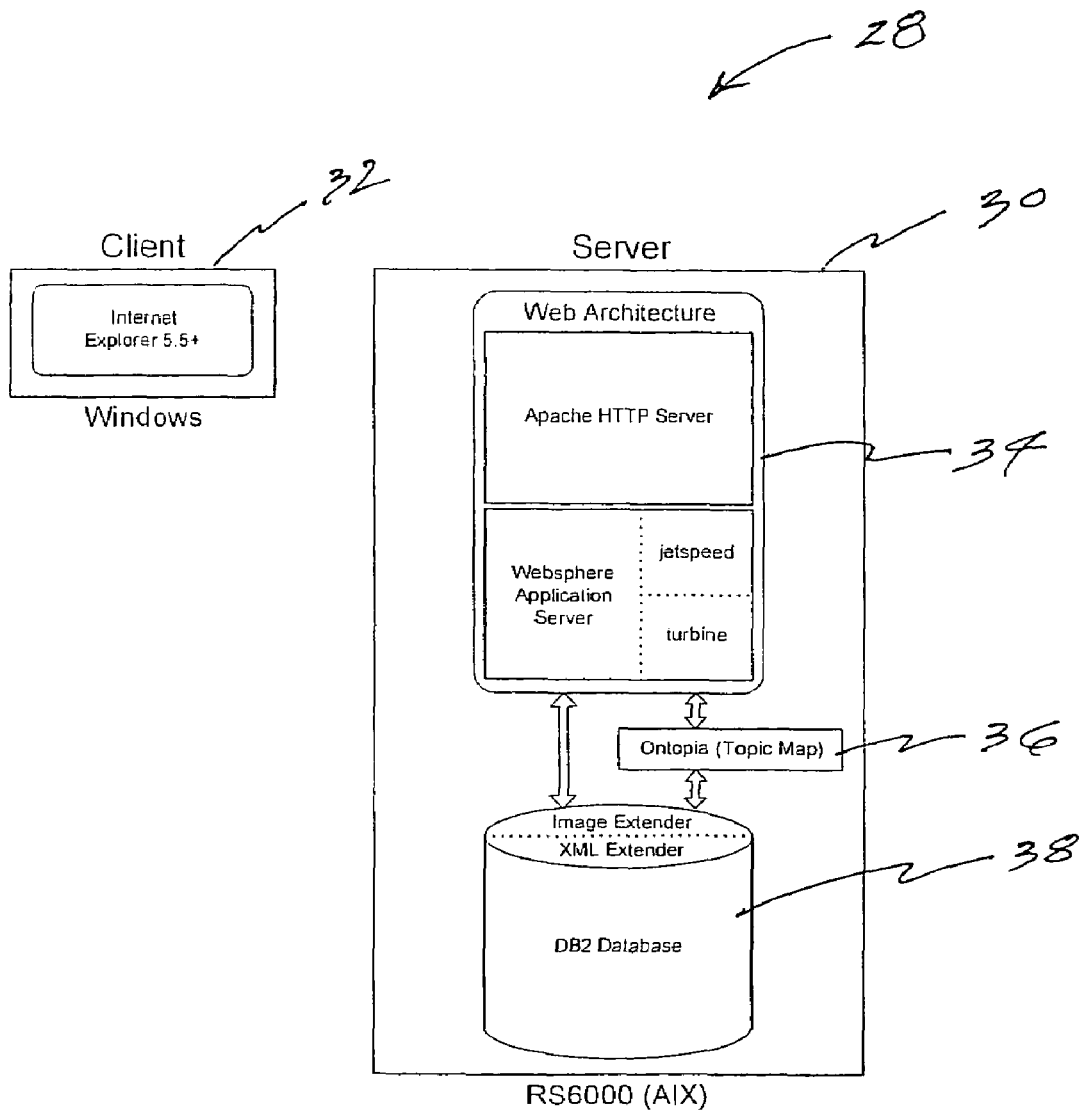
FIG. 3 depicts a System Online Architecture Chart illustrating one possible embodiment of the present system and method's hardware and software platform and a method of client deployment for specific products.

Referring now to FIG. 3, there is shown a chart illustrating one possible embodiment of a general on-line architecture 28 of the present system and method. This chart summarizes a hardware platform and software platform for deployment for the diagnostic reference system 20, the expert imaging center system 22, and continuing medical education system 24. Specific hardware and software elements illustrate one possible embodiment of the system, but many others are possible and likely as technology advances. The client utilizes web browser software 32 such as Internet Explorer™ version 5.5 or greater in a Windows™ or other environment, which can be deployed via the Internet, intranet, personal computer or desktop running with a local server. A server 30 is comprised of web architecture 34, a database 38, and a topic map 36. The web architecture 34 is comprised of an Apache HTTP™ server, a Websphere™ application server, and Jetspeed™ and Turbine™ components. The DB2 database 38 consists of DB2™ plus Image Extender™ and XML Extender™. The topic map 36 is implemented with Ontopia™ software. The hardware server platform in this example is RS6000 (AIX). None of the foregoing list is meant to be exhaustive or restricting on the system.

Figure 4:
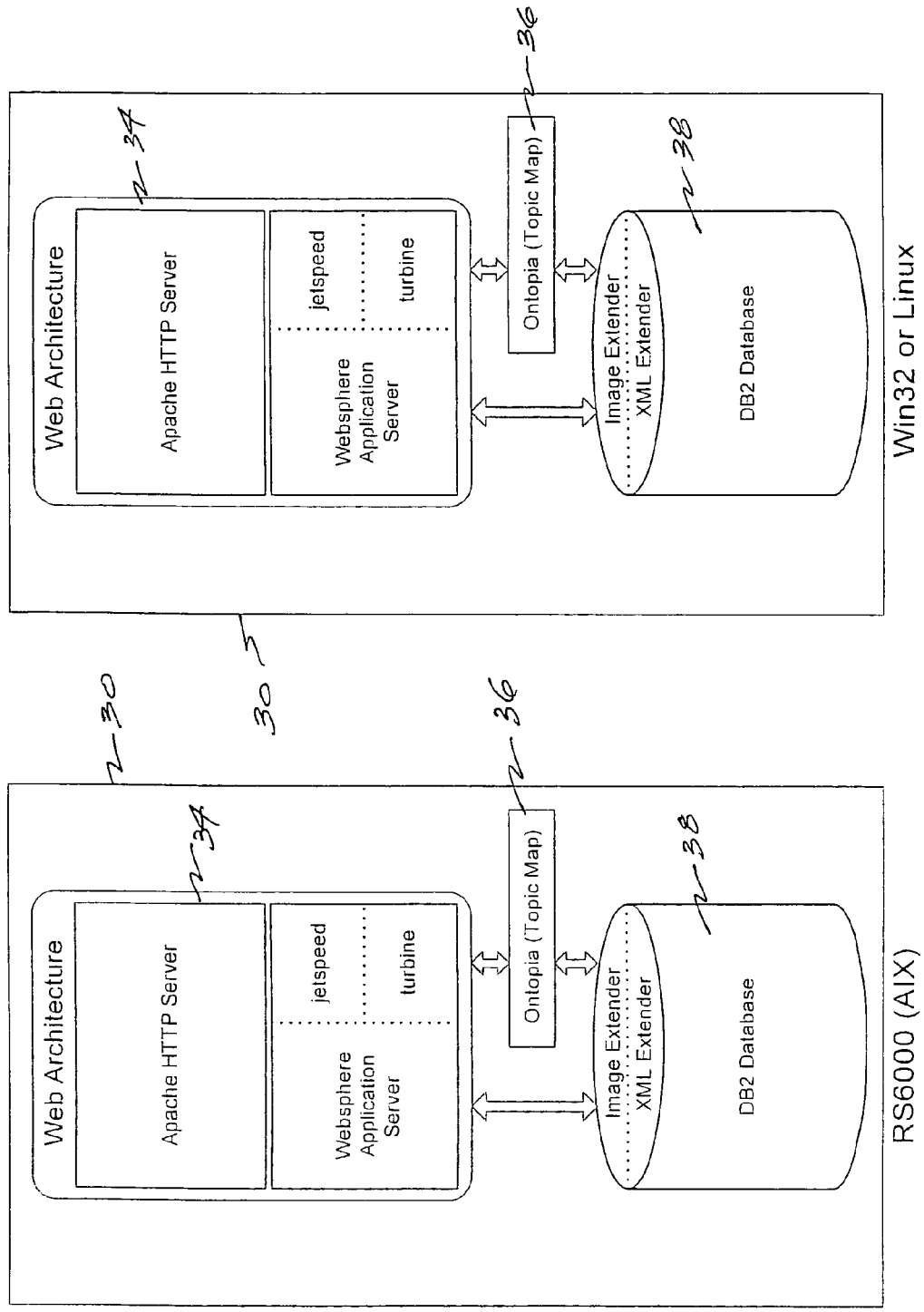
FIG. 4 depicts a System Online Architecture Chart illustrating one possible embodiment of the present system and method's hardware server platform options.

Referring now to FIG. 4, a diagram is shown illustrating the server of FIG. 3, with alternative platform Win 32 or Linux represented.

Figure 5:
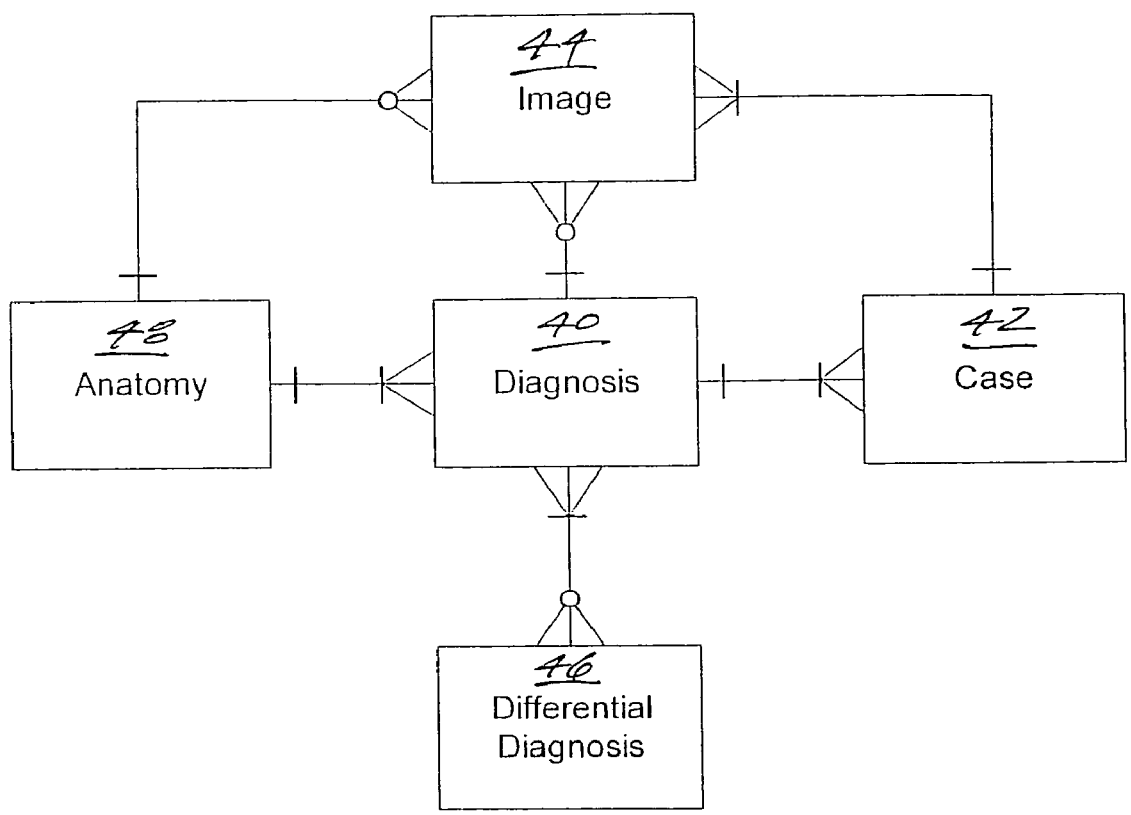
FIG. 5 depicts a Diagnosis Data Relationships Chart illustrating the relationships between a diagnosis and related data elements.

Referring now to FIG. 5, a diagram is shown that illustrates diagnosis data relationship between a diagnosis 40, which is considered to be a central feature of the present system and method, and related data elements. Each diagnosis 40 will have one or more cases 42. Each diagnosis 40 may have one or more images 44. Each diagnosis 40 may have one or more differential diagnoses 46. Each diagnosis will be related to one or more anatomy 48 categories. Each differential diagnosis 46 may have one or more diagnoses 40. Each case 42 will be related to only one diagnosis 40. Each case 42 will have one or more images 44. Each image 44 will be related to one case 42, one diagnosis 40 and/or one or more anatomy 48 categories. Each anatomy 48 may have one or more images 44. Each anatomy 48 will be related to one or more diagnoses 40.

Figure 6:
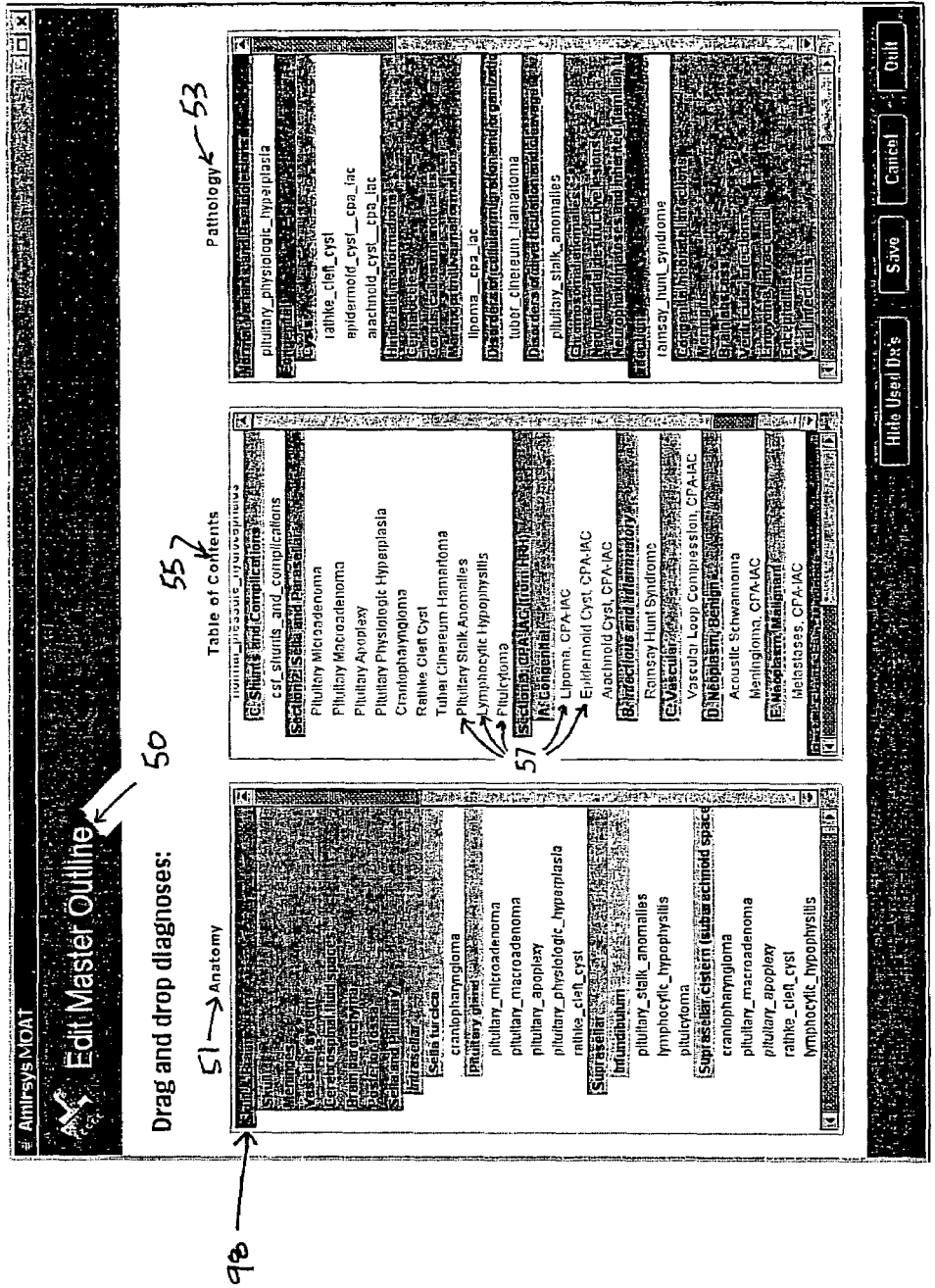
FIG. 6 depicts a Master Outline Screen according to one embodiment of the present invention.

Referring now to FIG. 6, a screen of a graphical user interface ("GUI") of the present system and method, to be negotiated by a user, is shown and displays a portion of a master outline 50. The master outline 50 is used to create a master index or "topic map" of the GUI. FIG. 6 illustrates a master outline 50 for the organ system 98. In this example the user has selected the "Skull & Brain" organ system. Each authoring project for a major organ system requires its own master outline 50, while projects that cross multiple organ systems, such as Pediatrics, use existing master outlines. The master outline 50 includes at least one organizational hierarchy. Two are shown in the example, namely anatomy 51 and pathology 53. A comprehensive list 55 ("Table of Contents") of unique diagnosis names 57 is also shown. Each diagnosis name 57 must stand alone (i.e., it must be complete when listed outside of its hierarchical context), must be unique within an organ system master outline 50, and must be unambiguous between organ system master outlines (e.g., "Chiari 1 malformation, brain" vs "Chiari 2 malformation, spine"). Also illustrated are the relationships between each diagnosis and their respective hierarchies. Master outlines 50 will vary in complexity. Some require database tools to generate; whereas others may be created using a text editor.

Figure 7:
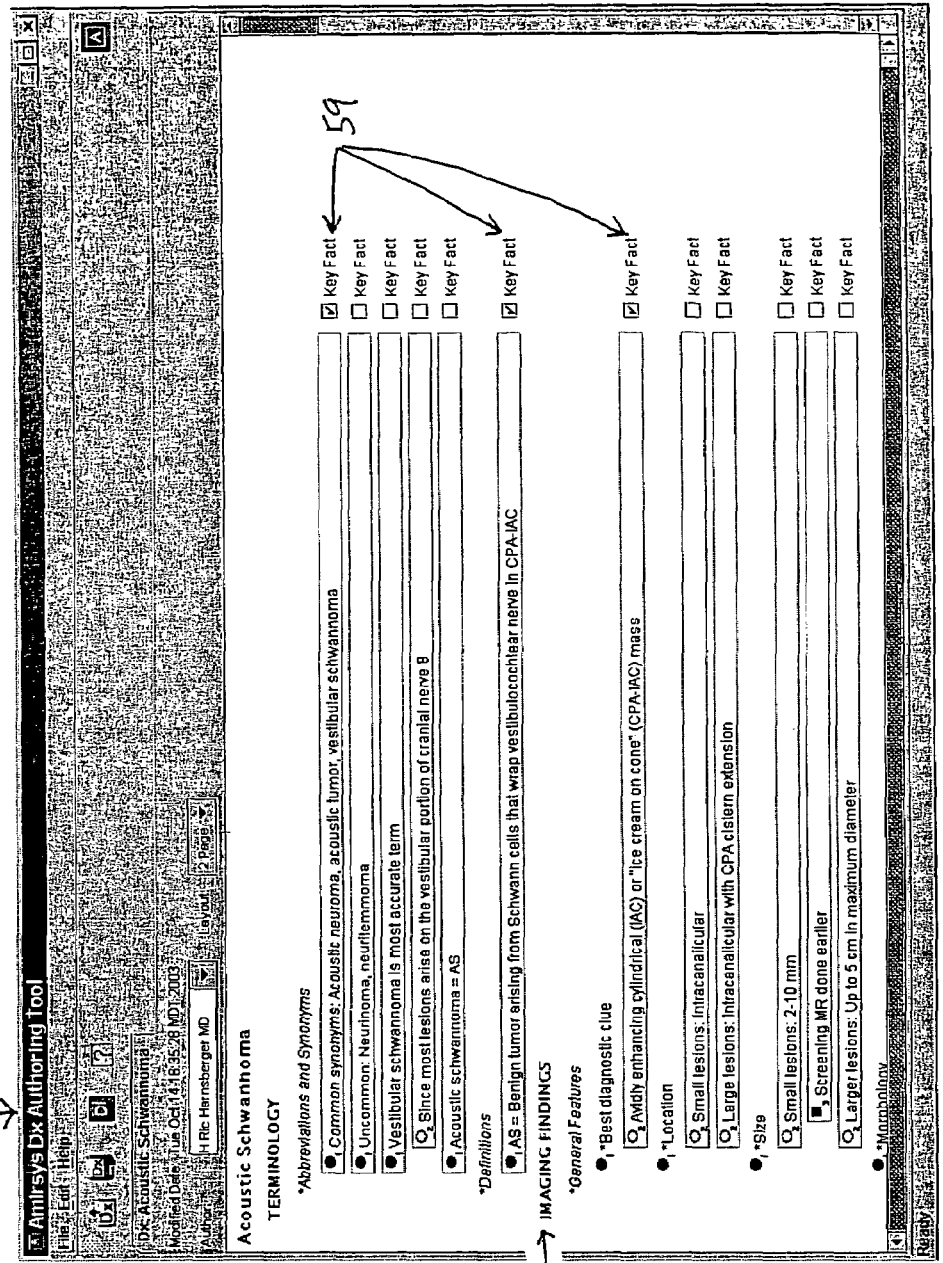
FIG. 7 depicts a Diagnosis Authoring Tool ("DAT") Diagnosis Screen according to one embodiment of the present invention.

Referring now to FIG. 7, there is shown a screen of the GUI which illustrates a portion of the diagnosis ("Dx") authoring tool ("DAT") 52. The DAT tool 52 provides for text entry of all fields for all diagnosis data elements, such as key facts 59, imaging findings 61, etc.

Figure 8:
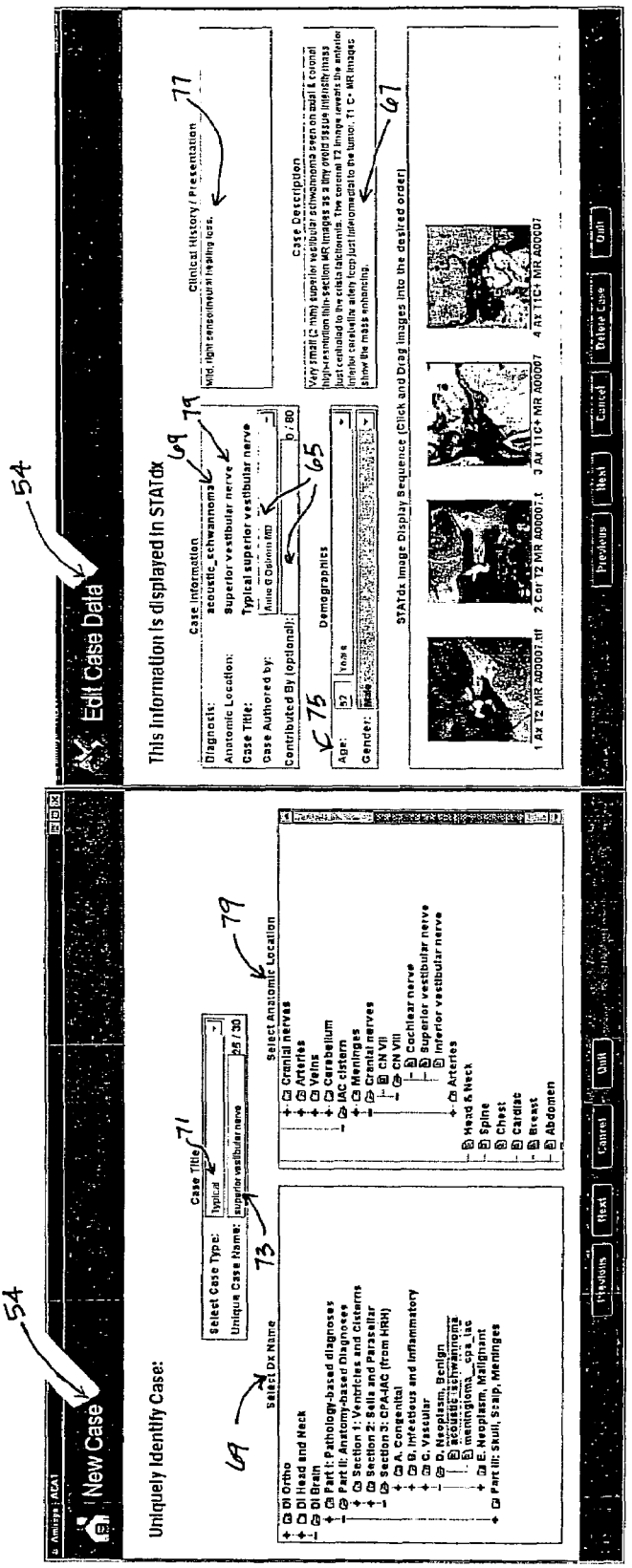
FIG. 8 depicts a Case Authoring Tool ("CAT") Case Screen according to one embodiment of the present invention.

Referring now to FIG. 8, there are shown two screens of the GUI which illustrates a case authoring tool ("CAT") 54 for entry and editing of images and text relating to case information. "Case information" includes author and contributor information 65 (in this particular illustration the case authored by is "Anne G. Osborn" has been selected), case description (author's note) 67, link to the pertinent diagnosis name 69 (in this particular illustration the diagnosis "acoustic schwannoma" has been selected), case type (composite, typical or variant) 71 (in this particular illustration the "typical" has been selected), unique case name 73 (in this particular illustration the "superior vestibular nerve" has been selected), generic patient demographics 75 (in this particular illustration the "age" as "52" and the "Gender" as "Male" has been selected), clinical history/presentation 77, and anatomic location 79 (in this particular illustration the "Superior vestibular nerve" has been selected).

Figure 9:
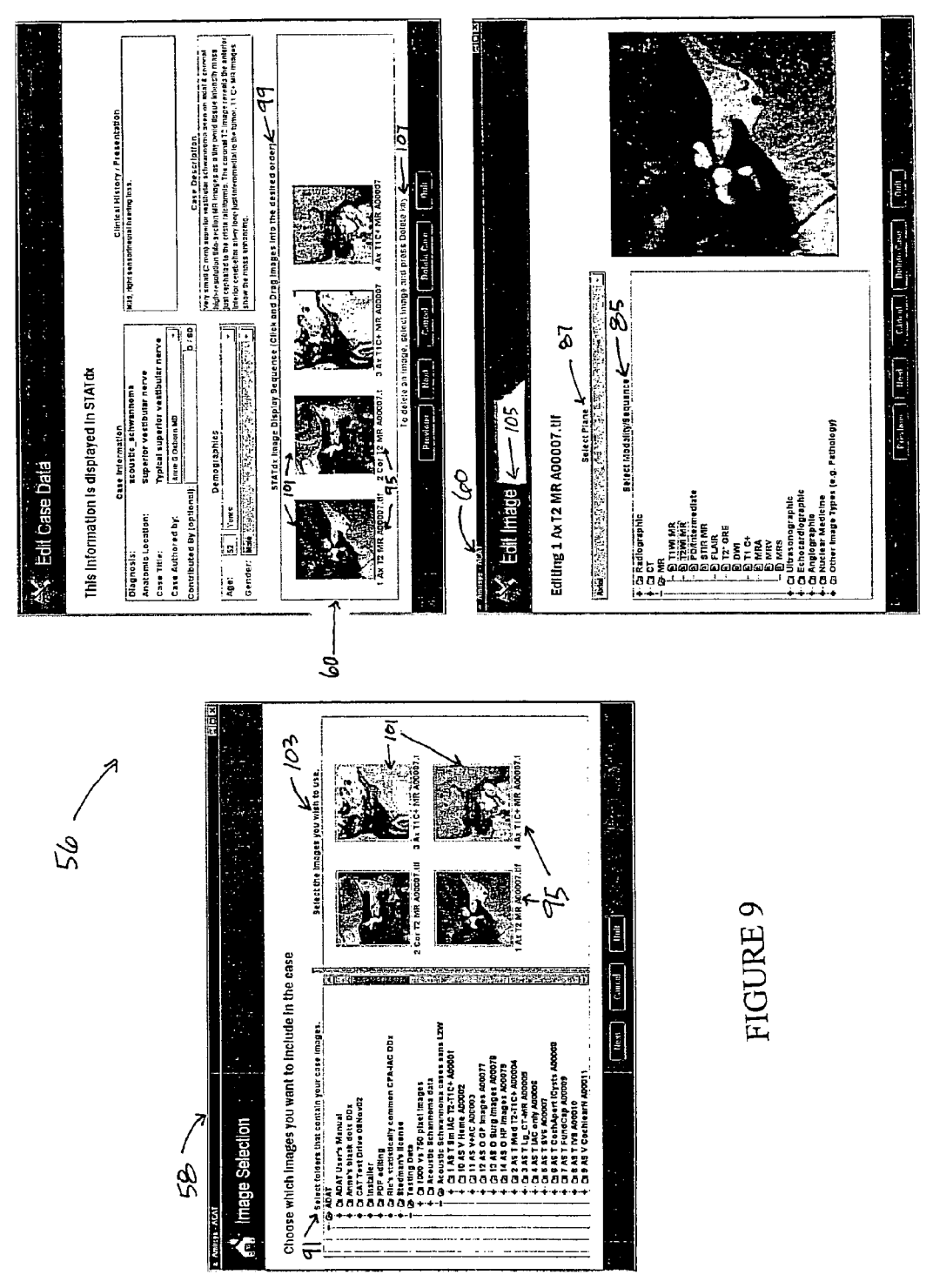

Referring now to FIG. 9, there are shown three screens of the GUI which illustrate a case authoring tool ("CAT") for image display 56. The CAT image display 56 includes entry 58 and image maintenance 60 tools. Image entry tools 58 provide a method for browsing through the computer file system to the original image file path 91 of an image, a thumbnail view 101 of images to choose from, and a method for adding 103 images to the case. Image maintenance tools 60 show current image file names 95, provide methods for defining the sequence of files 99 for all images in a case and deleting 107 an image from a case, and methods for editing 105 the image modality 85 and image plane 87 for each image.

Figure 10:
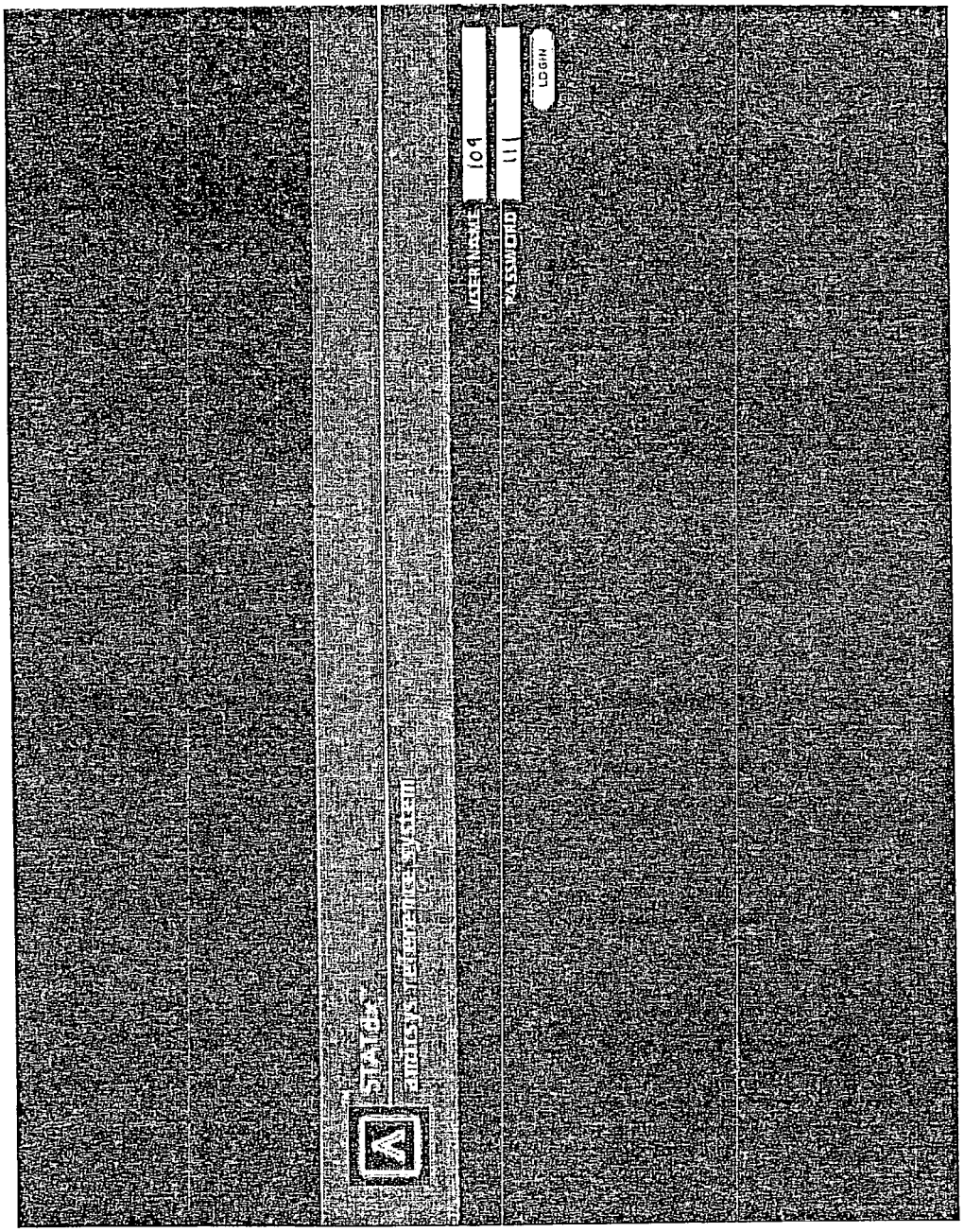
FIG. 10 depicts a User Entry Screen according to one embodiment of the present invention.

Referring now to FIG. 10, there is shown a screen of the GUI which illustrates a diagnostic reference system user entry tool 62. The diagnostic reference system user entry tool 62 displays an entry point for a user. This particular screen illustrates access by an online user and includes a window for entering a username 109 and a password 111. It is noted that the screen depicted is used in connection with an online user, but the screen is applicable to offline uses and access as well.

Figure 11:
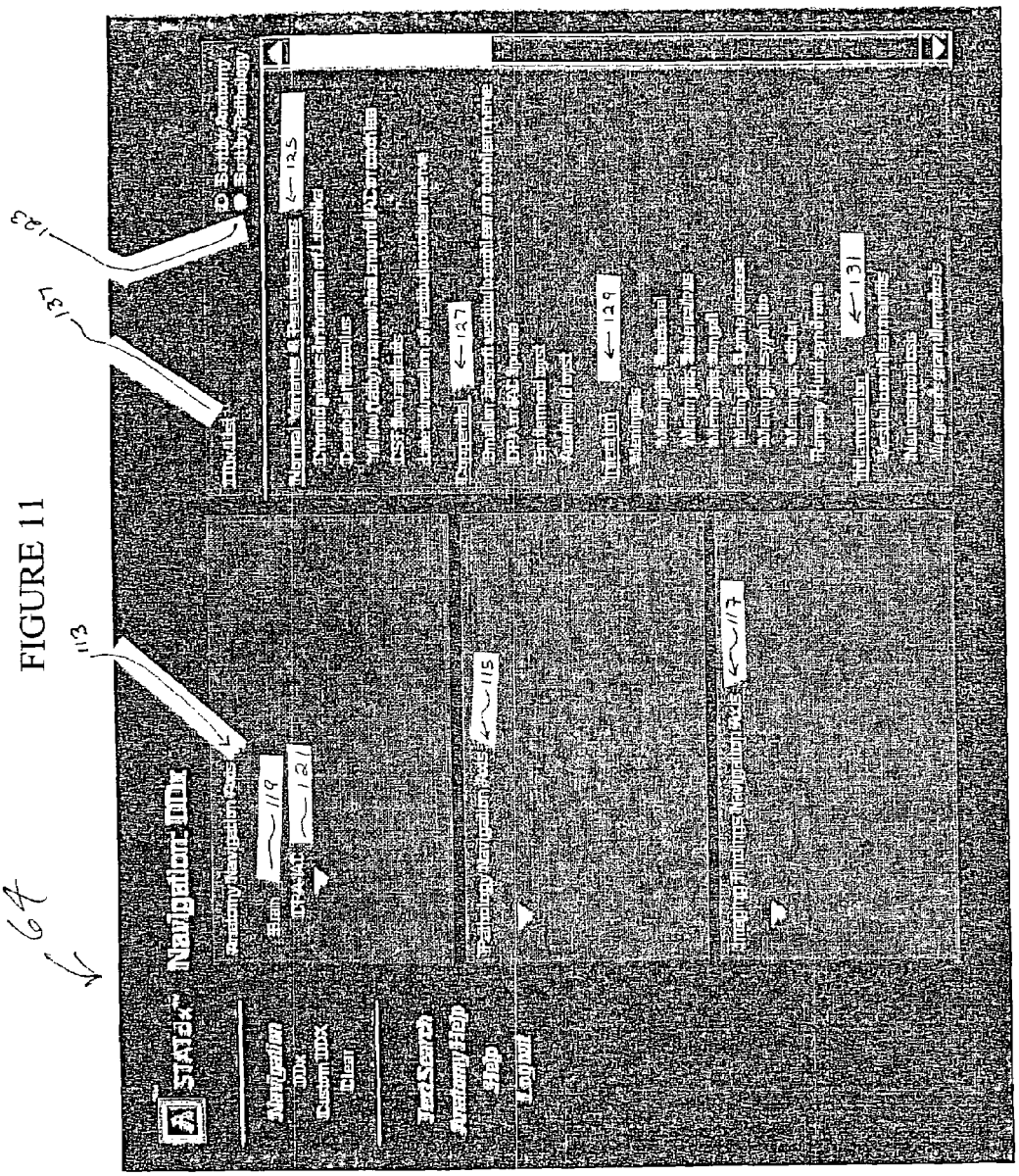
FIG. 11 depicts a three axis Navigation Screen with one axis activated according to one embodiment of the present invention.

Referring now to FIG. 11, there is shown a screen of the GUI which illustrates a diagnostic reference system user navigation tool 64. The diagnostic reference system user navigation tool 64 is a three axis navigational tool which in this example indicates only one axis in active use; more particularly, this screen illustrates the system's ability to allow a user to navigate multi-dimensional hierarchy through the comprehensive diagnosis list in the content database 12 (FIG. 1) via navigation axes of anatomy 113, pathology 115 and/or image findings 117, and then sort the resulting differential diagnosis, or list of potential diagnoses, by either the anatomy or by pathology categories. This screen illustrates a user choice of the anatomy navigation axis 113 with selection of first level anatomy "Brain" 119 and second level anatomy "CPA-IAC" 121 categories. The user has also selected "sort by pathology" 123 and the system has shown the differential diagnosis sorted by first level pathology categories including "Normal Variants & Pseudolesions" 125, "Congenital" 127, "Infection" 129, and "Inflammation" 131. Note that the differential diagnosis list 137 is a very long list scrolling off the bottom of the page.

Figure 12:
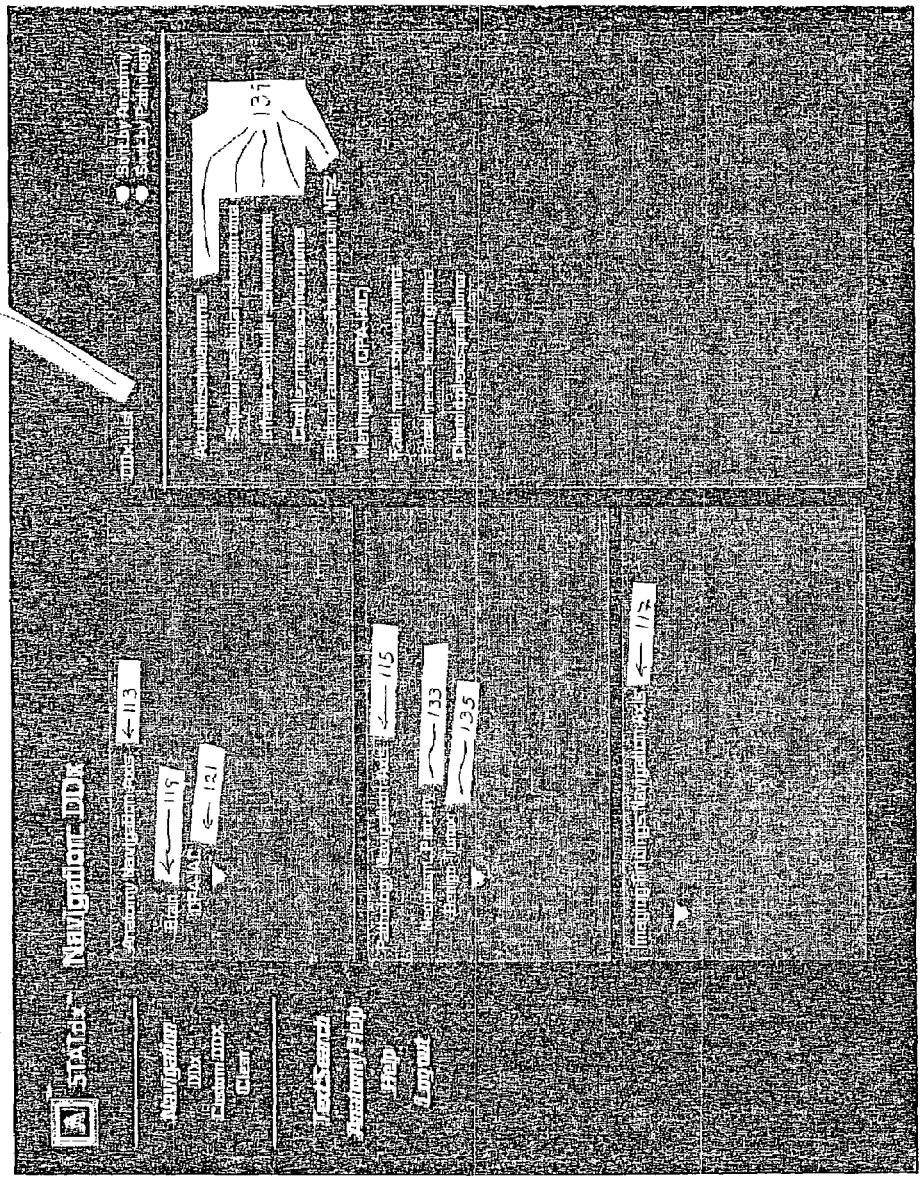
FIG. 12 depicts a three axis Navigation Screen with two axes activated according to one embodiment of the present invention.

Referring now to FIG. 12, there is shown a screen of the GUI which illustrates a dual axis diagnostic reference system user navigation tool 66. This tool 66 demonstrates the system's ability to shorten the differential diagnosis by adding a second navigation axis. Here, a user has elected to add the additional pathology axis 115 to the navigation. The user has selected the pathology first level "Neoplasm, Primary" 133 and second level "Benign Tumor" 135 categories while simultaneously navigating anatomically. The resulting differential diagnosis list 137 is now much shorter, including only nine differentials 139 shown. This shortened list is significantly more useful to make an accurate diagnosis than a longer list. After navigating to identify a diagnosis of interest, the user clicks on the diagnosis name 139 to go to the diagnosis screen in FIG. 15.

Figure 13:
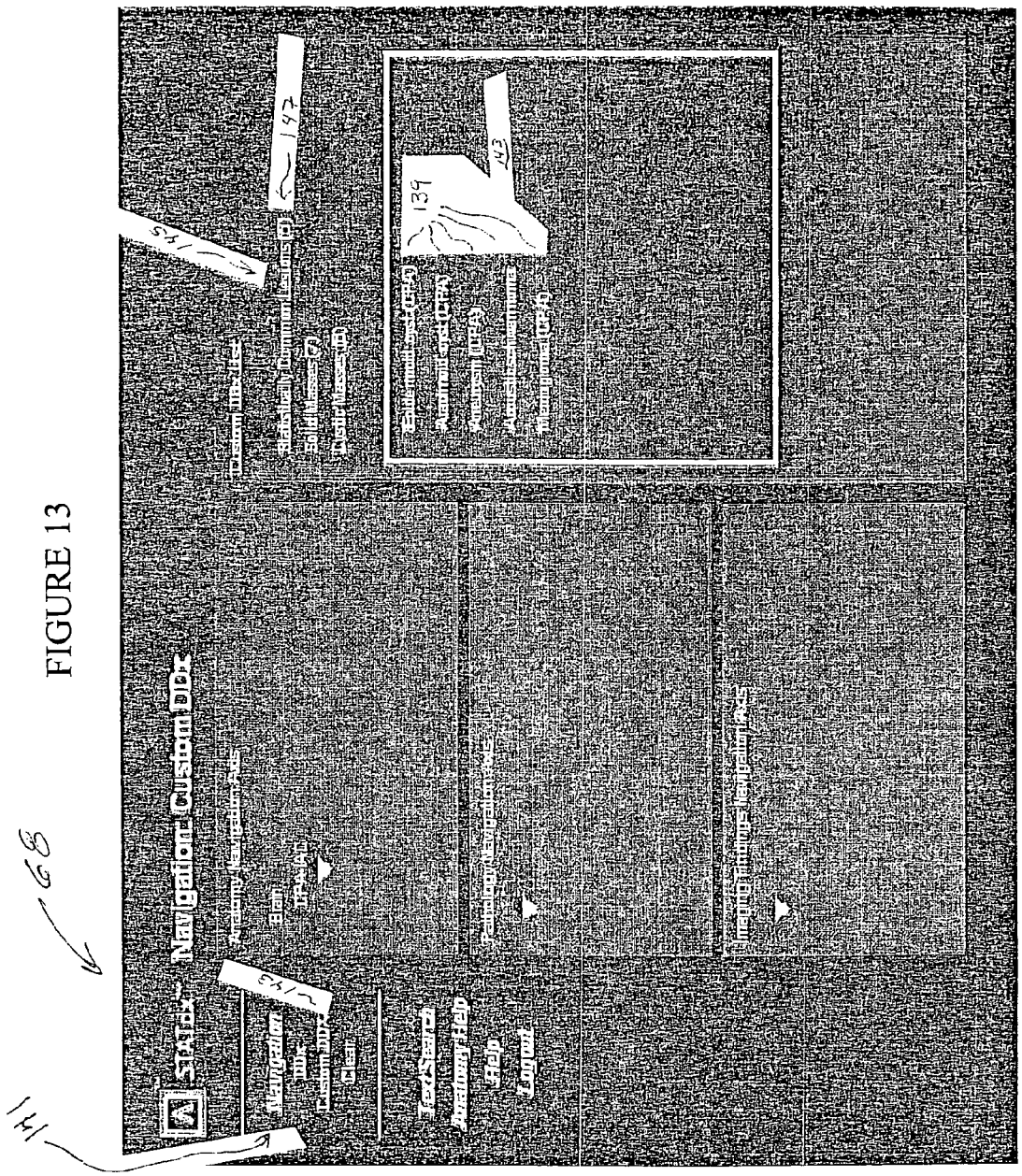
FIG. 13 depicts a Custom Differential Diagnosis Screen according to one embodiment of the present invention.

Referring now to FIG. 13, there is shown a screen of the GUI which illustrates a custom differential diagnosis navigation tool 68. This tool 68 can allow a user to create a custom differential diagnosis. By selecting "Custom DDx" 143 from the menu 141, the user is presented with a list of custom differentials 143 for the current navigation context grouped thematically by an expert, luminary author. In this example the user has choices 145 from "Statistically Common Lesions", "Solid Masses" and "Cystic Masses". The user has chosen "Statistically Common Lesions" 147 and the system has presented a list of differentials 143 including "Epidermoid cyst", "Arachnoid cyst", "Aneurysm", "Acoustic schwannoma" and "Meningioma". After navigating a custom DDx to identify a diagnosis of interest, the user clicks on the diagnosis name 139 to go to the diagnosis screen in FIG. 15 below.

Figure 14:
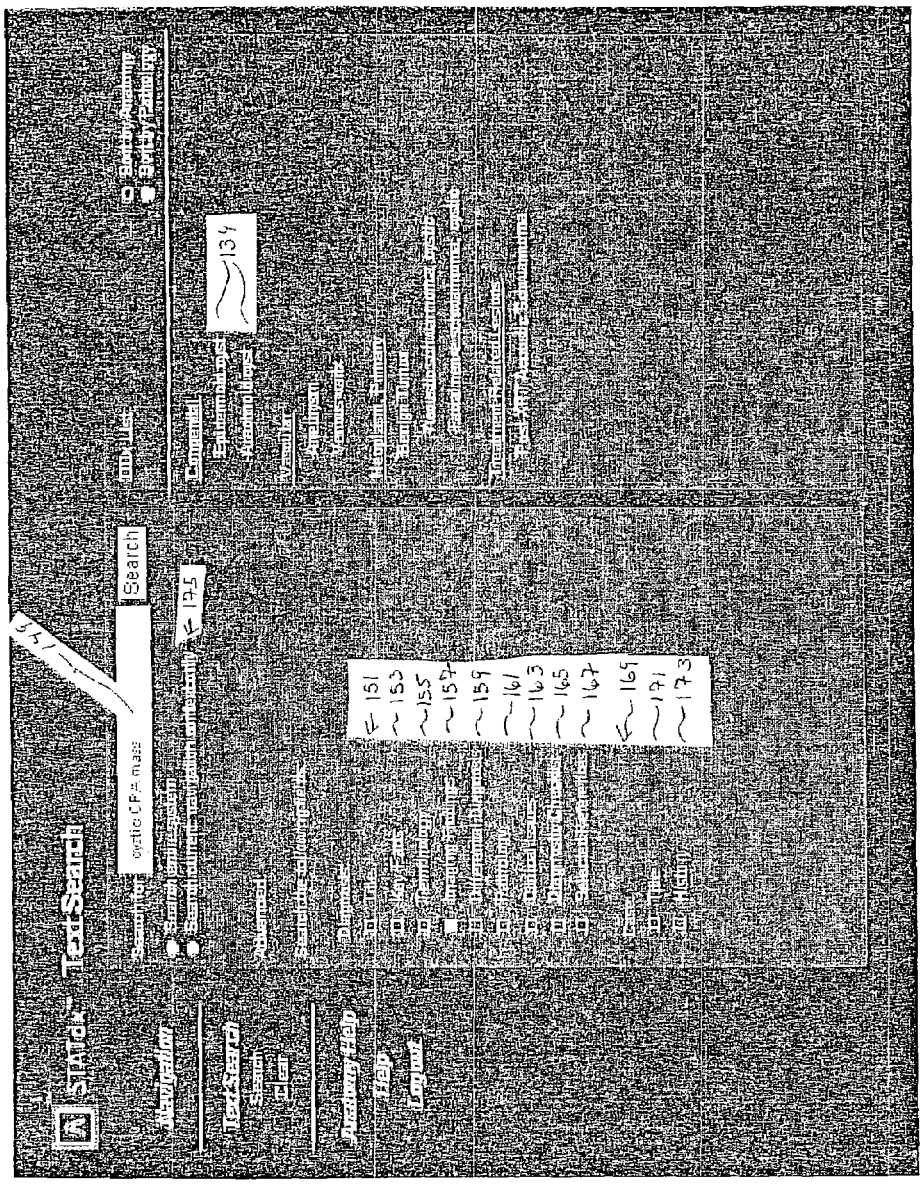
FIG. 14 depicts a Text Search Screen according to one embodiment of the present invention.

Referring now to FIG. 14, there is shown a screen of the GUI which illustrates a text search tool 70. The text search tool 70 allows the user to search for text in specified database fields. In this example, the user has elected to search for the text string "cystic CPA mass" 149. The search screen also illustrates the ability of a user to utilize advanced search criteria in the fields of diagnosis (including title 151, key facts 153, terminology 155, imaging findings 157, differential diagnosis 159, pathology 161, clinical issues 163, diagnostic checklist 165, selected references 167) and by cases 169 (including title 171 and history 173). In this case the user has selected the option 175 to constrain the search to the current navigation context and "imaging findings" data fields in the database. After searching to identify a diagnosis of interest, the user clicks on the diagnosis name 139 to select a specific diagnosis to consider and is then sent to the diagnosis screen in FIG. 15 for the selected diagnosis.

Figure 15:
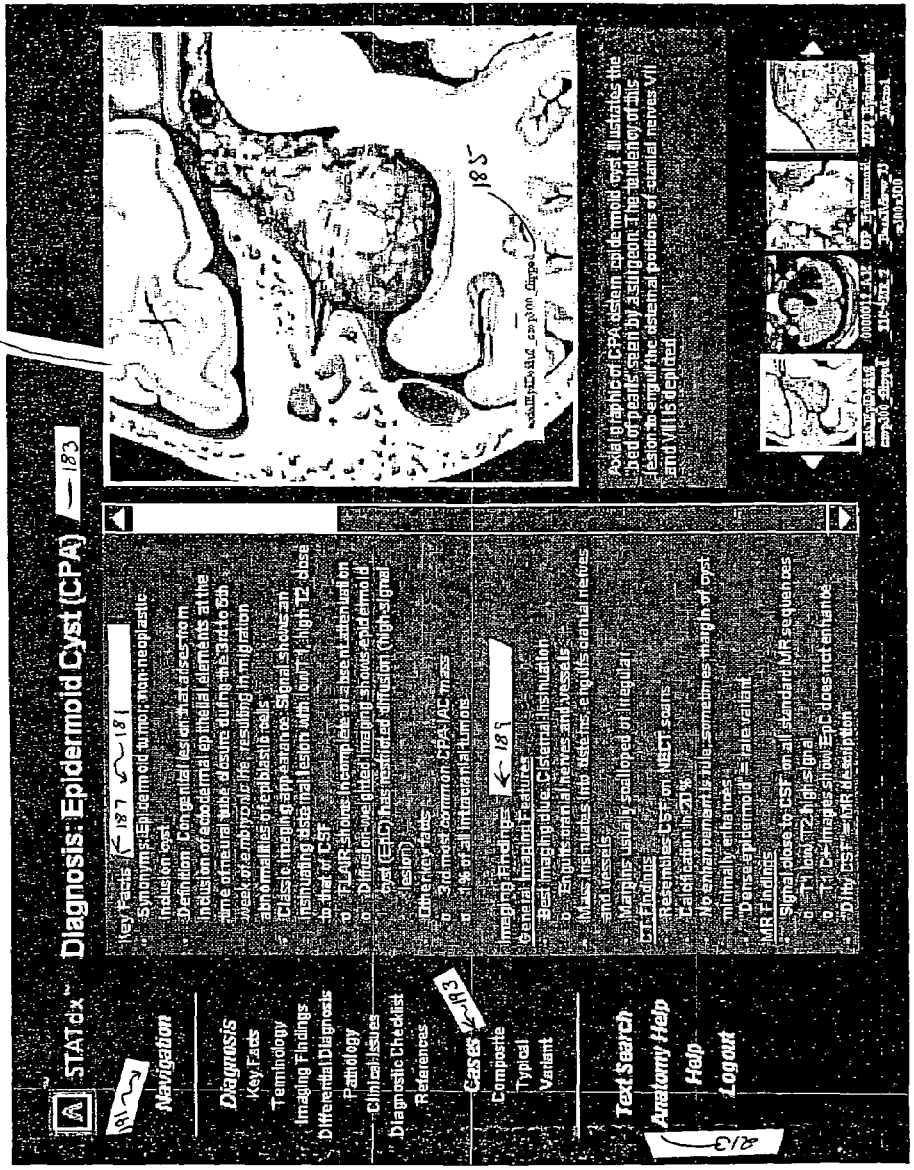
FIG. 15 depicts a General Diagnosis Screen according to one embodiment of the present invention.

Referring now to FIG. 15, there is shown a screen of the GUI which illustrates a diagnosis display 72. The diagnosis display 72 includes an image 177 having substantial graphic detail. The displayed image 177 is selected from a scrollable strip of multiple image thumbnails 179 related to the selected diagnosis. Detailed textual information about the diagnosis 181 is also provided.

In this example, the user has selected the diagnosis "epidermoid cyst (CPA)" 183. The images thumbnails 179 allow the user to quickly scroll and toggle among multiple different images of this specific diagnosis. Once an image thumbnail 179 is selected (in FIG. 15, as indicated by the highlighting around the image the left most image of the four thumbnails is selected), then that image 177 is shown in a much larger size and with a detailed image caption 185. The text column 181 near the center of the screen provides a detailed description of the diagnosis, including key facts 187, imaging findings 189 and other information. The menu 191 at left provides access to cases 193 related to the diagnosis. Clicking any of the cases menu options switches to the case screen. The user can select from Cases 193 examples of any of three categories of cases: such as composite, typical and variant or other categories.

Figure 16:
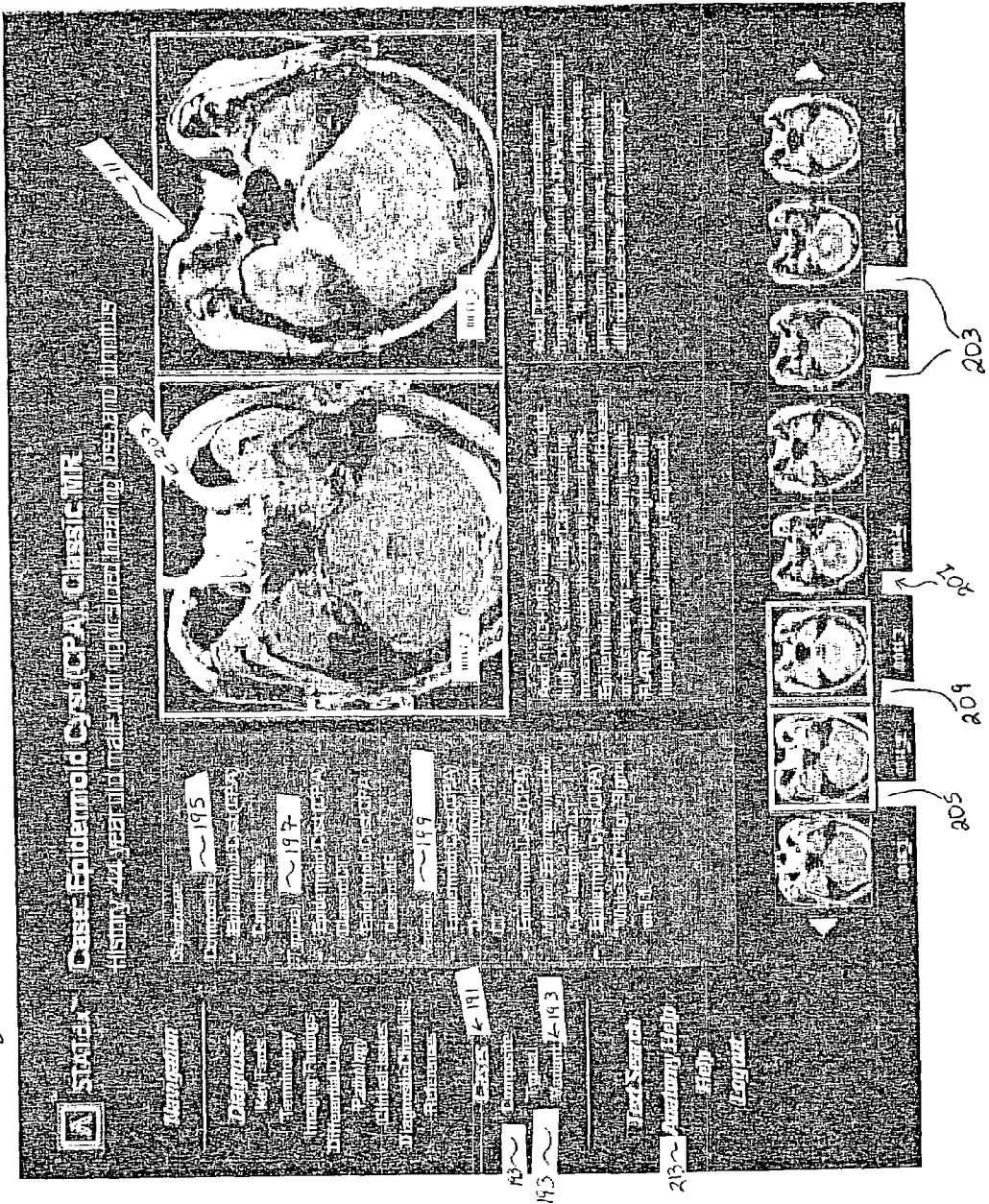
FIG. 16 depicts a Case Screen according to one embodiment of the present invention.

Referring now to FIG. 16, there is shown a screen of the GUI which illustrates a case display tool 74. The case display tool 74 lists composite 195, typical 197, and variant 199 cases of a selected diagnosis. The screen also illustrates the system's ability to juxtapose relevant images with the text description. At the bottom of the screen is a scrollable list of image thumbnails 201 that relate to the selected case. A user can scroll and select any two thumbnails 203 and a larger version of the selected images will appear above in the center right portion of the screen. In this example, a user has selected at the bottom the second from left thumbnail 205 which is then displayed above to the left in the larger image 207 as well as selected at the bottom the third from the left thumbnail 209 which is then displayed at the top right in larger format 211.

Figure 17:
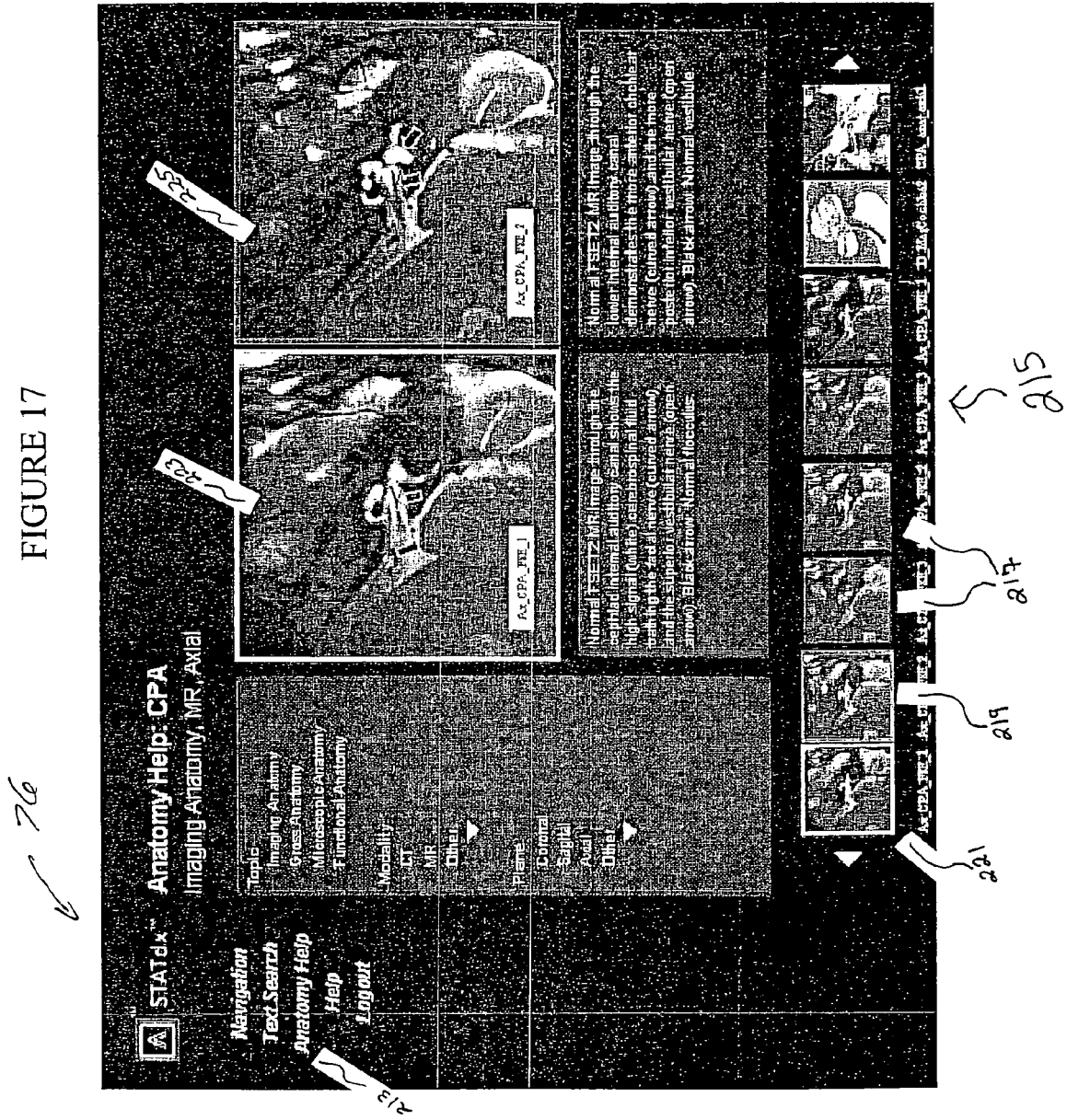
FIG. 17 depicts an Anatomy Help Screen according to one embodiment of the present invention.

Referring now to FIG. 17, there is shown a screen of the GUI which illustrates an anatomy help screen 76. The anatomy help screen 76 may be accessed by clicking on an anatomy help menu item 213 in either the diagnosis screen 72 (FIG. 15) or case screen 74 (FIG. 16). This screen illustrates the system's ability to allow the user to select from normal anatomy topics, imaging modality, and imaging planes. At the bottom of the screen is a scrollable list 215 of image thumbnails 217 that relate to normal anatomy related to the existing diagnosis. A user can scroll and select any two thumbnails 217 and a larger version of the selected images will appear above in the center right portion of the screen. In this example, a user has selected at the bottom the far left thumbnail 221 which is then displayed above to the left in the larger image 223 as well as selected at the bottom the second from the left thumbnail 219 which is then displayed at the top right 225 in larger format.

Figure 18:
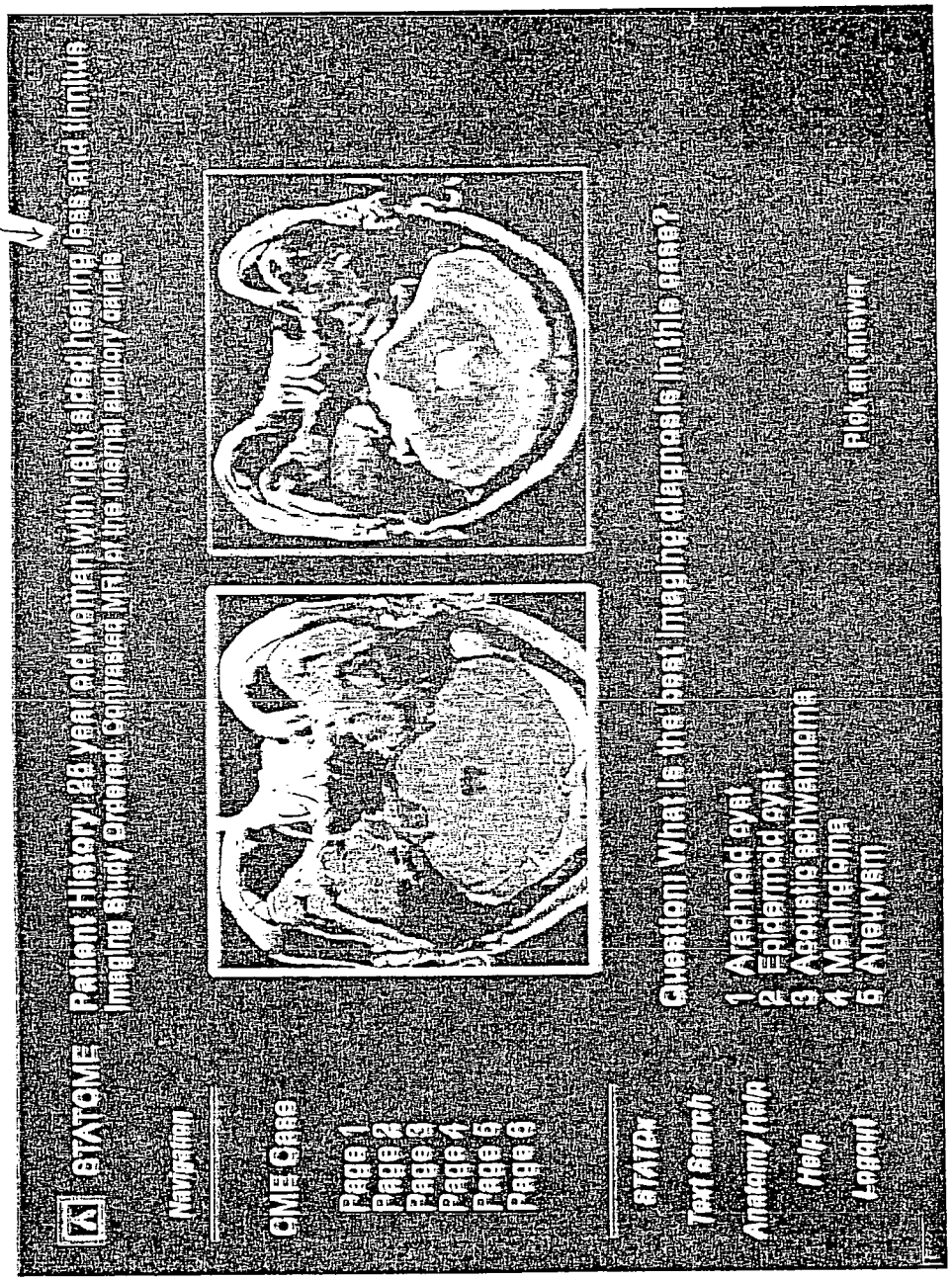
FIG. 18 depicts a continuing medical education ("CME") Screen according to one embodiment of the present invention.

Referring now to FIG. 18, there is shown a screen of the GUI which illustrates an example of a continuing medical education ("CME") product 78. The patient history review 78 function is an example of a test question for a certified program of continuing medical education for medical personnel. In conjunction with, or independent of, the diagnostic reference system 20, the continuing medical education product 78 can track a user's time while accessing a diagnosis, case, or anatomy help topic. The content database 12 (FIG. 1) may be updated with this information and then present the user with a series of test questions 227, track the user's test performance, and grant continuing medical education credit when a test is passed.

Figure 19:
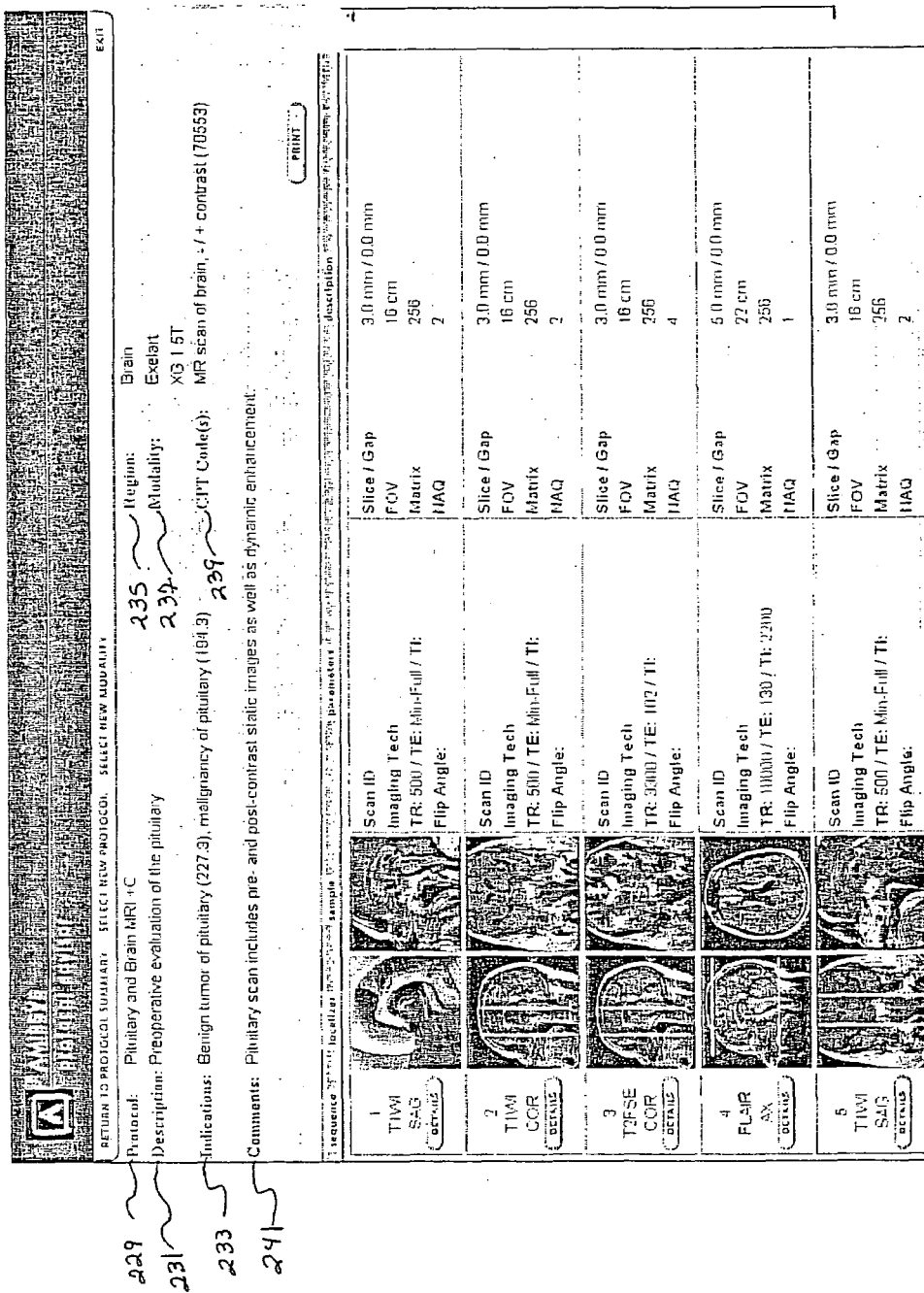
FIG. 19 depicts a series of protocols for an expert imaging center ("Protocol Advisor") Screen according to one embodiment of the present invention.

Referring now to FIG. 19, there is shown a screen of the GUI which illustrates an example of the expert imaging center protocol advisor product 22 (FIG. 1) that provides critical imaging protocols, validated procedures and research guidelines to the user through expert-validated user protocols. User protocols can be provided to all imaging modalities (e.g., MRI, CT, x-ray, etc.). A user can select the protocol 229, description 231, indications 233, region 235, modality 237, CPT code 239, and enter comments 241. In this example, a user has selected at the top on the far left the protocol 229 "Pituitary and Brain MRI+C" from a list of master protocols. The user must also select from a master list in the invention the region 235 of the body being imaged and the modality 237 of the imaging. In this example, the region 235 selected was "Brain" and the modality 237 selected was "Exelart XG 1.5T". Having made the selections, the invention then automatically provides information to the user regarding indications 233, CPT codes 239 and comments 241. The invention also automatically produces the optimal sequences to be imaged, including specific information 242 regarding slice/gap, FOV, matrix, NAQ and other information. If the user desires even more detailed information regarding how to optimize a particular sequence, the user may click on the details 238 button.

Figure 20:
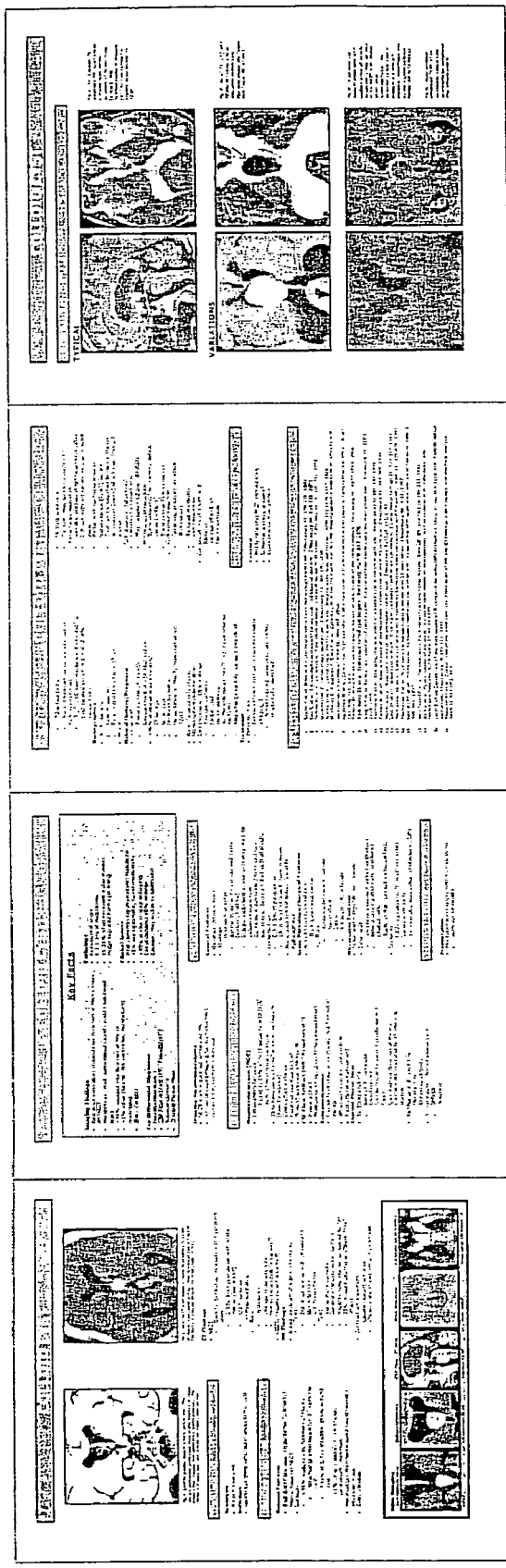
FIG. 20 depicts a Diagnostic Imaging Product in Print Form according to one embodiment of the present invention.

Referring now to FIG. 20, there is shown a sample diagnostic imaging product in print media form 82. Diagnostic imaging printed media products 86 (FIG. 1) may be output from the content database 12 (FIG. 1) as printed media in a standard textbook trim size (or other sizes) with approximately 250 (or higher or lower) diagnoses per book for a total of approximately 1,000 pages. In this example, a four-page diagnosis 243 has been output and includes expanded content relative to a designated diagnosis. The example 243 indicates output in the format of bulleted text and includes sections for key facts, terminology, imaging findings, differential diagnosis, pathology, clinical issues, diagnostic checklist, images and selected references.

Figure 21:
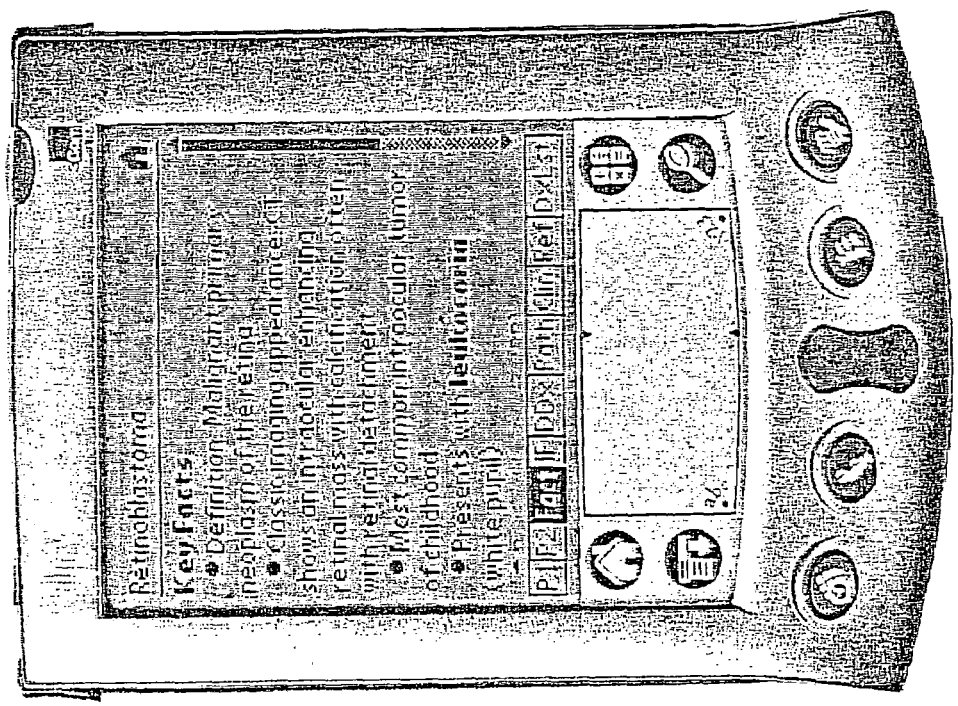
FIG. 21 depicts a POCKETRADIOLOGIST® Product in PDA Form according to one embodiment of the present invention.

Referring now to FIG. 21, there is shown a PDA product 84 for PocketPC and Palm in PDA form 88 (FIG. 1). In this example, a user has selected a diagnosis of "Retinoblastoma" 245. The user has selected to examine the "Fact" 247 section of the information by touching the "Fact" 247 on the screen at the bottom of the PDA device. The PDA device then displays the "Key Facts" 249 textual content to summarize the most important data regarding a retinoblastoma diagnosis.

Method of Operation

The method of operation of the Invention involves many steps. Some steps must be taken in a specific order of events, while other steps may be taken in varying order of events. The user of the Invention (in this embodiment an author) must first create a master outline using the master outline authoring tool ("MOAT") (see FIG. 6). The author needs to create linkages between specific medical diagnoses 55 (like Lipoma 57) and various anatomy 51 areas of the body (like the Skull & Brain 98), and to a specific pathology 53 that relates to the anatomy and diagnosis selected.

The second major activity required by the Invention of the author is for the selection and annotation of cases and the medical images illustrating and supporting each case. The case authoring tool ("CAT") (FIGS. 8 and 9) is designed to assist the author/user with this task. The author can readily import multiple images and cases into the CAT tool and label, annotate and sequence all cases and images.

When the author has created his master outline and completed the CAT process, then thirdly the author must create the comprehensive description of each medical diagnosis. The author utilizes the diagnostic authoring tool ("DAT") to achieve this task (see FIG. 7). The DAT tool ensures that all data input by the author will be done so in a consistent, templated format. The author must complete all "blank" areas in the DAT tool fields. The author has some latitude to add and subtract additional fields (e.g., in Imaging Findings 61 the author has elected to describe the locations of both "small lesions" and "large lesions"). The author must decide which of all facts included in the comprehensive description of the diagnosis will qualify as "key facts" 59 and must select each key fact by clicking on the appropriate box. Images for the diagnosis are selected from cases of that diagnosis previously created with CAT.

Upon completion by the author/user, all the information input by utilizing all of the Invention's tools (CAT, DAT and MOAT) are transferred into the content database 12 (see FIG. 1). During the process of transfer the data is reviewed by both by utilizing automated functions as well as by administrative and professional staff to ensure data integrity and accuracy.

Print and PDA products can readily be created by production staff by utilizing the Invention's content database 12 (see FIG. 1). The production staff can elect to create, for example, a Palm PDA product 88. The production staff queries the content database 12 and selects the data that relates to the subject of a particular product. For example, if the production staff wished to create a Palm PDA product on the subject of the top 100 diagnoses that occur in radiologic imaging in the area of the brain, the production staff could select all such data. The Invention then will automatically generate a Palm PDA product that has all such data in a pre-formatted, templated output ready for entry into the Palm PDA software product. These Palm PDA images will then be displayed on a concise format on the PDA devices 84 (FIG. 21).

A user may also elect to view the content in the content database 12 (see FIG. 1) from the online suite 21 of products. One such method of accessing the content database 12 from the online suite 21 is via the diagnostic reference system 20(a). The diagnostic reference system 20(b) may also be utilized via the remote suite 23. The user accesses the Invention by providing their name 109 and password 111 in the diagnostic reference system user entry tool 62 (FIG. 10). The user can then proceed to utilizing the online 20(a) and/or remote 20(b) diagnostic reference system application and content database 12 via a series of GUI access points. For example, the user can select to navigate by anatomy 113 (FIG. 11) and find all diagnoses that occur in the selected areas of anatomy (e.g., in the CPA-IAC 121 region of the Brain 119). By making these anatomical selections, the Invention then displays to the user from the differential diagnosis list (DDX) 137 sorting all possible diagnoses by pathology classification groups (e.g., Normal Variants 125, congenital 127, infection 129 and inflammation 131). The user could also decide to also navigate the potential list of differential diagnoses by also utilizing the pathology navigation axis 115 (FIG. 12). For example, the pathology may be selected to indicate that it s a neoplasm, primary 133 and with a subset of benign tumor 135. By utilizing this additional navigation axis feature of the Invention, the user has greatly reduced the number of possible differential diagnoses to a much shorter list of possibilities 139. The Invention also allows the user to utilize its custom DDx navigation 68 (FIG. 13) features. If a user desires to instead search using text, the Invention allows for text search 70 (FIG. 14). For example, if the user believed that the condition was possibly a cystic CPA mass 149, the Invention can then search the content database 12 to locate all diagnoses that match this text search criteria and will display the results 139. In this example, the Invention has displayed two possible congenital diagnoses 139: epidermoid cyst and archnoid cyst. The user can then quickly access the content database 12 to more closely examine all relevant information regarding the diagnosis 72 (FIG. 15), in this example the diagnosis of epidermoid cyst 183. The invention then displays all key facts 187, 181, imaging findings 189, imaging examples 179 and color illustrations 177 as appropriate to fully explain and give examples of the diagnosis. If the user wishes to see even more detail regarding a potential diagnosis, the user can review detailed case examples 74 (FIG. 16) of each selected diagnosis. The user can then view cases from a wide list of possibilities, including composite 195, typical 197, variant 199 and other. The user can also view many thumbnail sized images 205, 209, 201, 203 as examples of the diagnosis in a variety of cases and select any image to enlarge 207, 211. The Invention also allows the user to access the content database 12 to learn detailed information regarding normal anatomical imaging 76 (FIG. 17). After selecting the "Anatomy Help" 213 feature, the Invention then allows the user to access detailed information regarding imaging anatomy by both modality and plane.

The Invention also contemplates that a user may wish to access the content database 12 to gain continuing medical education ("CME") units. This can be achieved both through the online suite 24(a) (FIG. 1) and/or by a remote suite 24(b). It is contemplated that a user will utilize a CME feature 78 (FIG. 18) while reviewing a particular patient case 227. The Invention will then pose certain inquiries to the user on the subject and if the user answers the questions correctly, the user will receive CME credits.

It is also contemplated that the Invention will be utilized to assist users to determine the optimal imaging protocols for conducting imaging studies of patients. This protocol advisor 80 (FIG. 19) feature can be used by radiologists, other imaging professionals and imaging technical staff. The user can select from a list of protocols such features as are appropriate for the patient study to be conducted (e.g., identify the body region 235, imaging modality 237, CPT codes 239 and protocol 229. The Invention then produces from the content database 12 the description 229, indications 233, comments 241 and all imaging sequences with protocols 242. If even greater protocol details are desired, the user can access the information via the "details" choice 238.

DEFINITION OF TERMS

Body of Knowledge—is any information gathered on a particular subject matter, which can be found in a variety of forms: books, newspapers, periodicals, theses, consortium notes, symposia dictations, and/or any other scholarly or independent works.

Diagnostic Authoring Tool ("DAT")— is a tool for that allows an author to enter text content compatible with digital database information, including diagnosis, key facts, imaging findings.

Case Authoring Tool ("CAT")—is a tool that allows an author to enter case description, link to pertinent diagnostic name, case type, date of imaging study, generic patient demographics, generic case history and publication history, and other information.

Content Smart—the portion of the present authoring system and method utilized currently with print and PDA production that allows the database to be filled with information contained in other formats (such as Word) and allows the extraction of data from the database to create directly a print or PDA format output.

Continuing Medical Education ("CME")— is a program of education provided to physicians and other health care providers.

Electronic Book—is a book represented in electronic media, not hard bound in paper, typically stored in a computer or PDA.

Electronic Medical Reference Title—is a title that is listed in electronic form, i.e. a title that represents the actual reference, which can be selected from a list of other electronic references listed, such as a book on a library shelf.

Ontology—a formally expressed representation of a certain body of knowledge.

PDA—personal digital assistant.

Tertiary forms of Information—books and other forms of information that usually contain information that was already out-dated at the time of publication.

Topic Map—Topic maps are a developing technology first described in ISO/IEC 13250:2000 and more recently extended into XML format in the XTM specification. The purpose of a topic map is to convey knowledge about resources through a superimposed layer, or map, of the resources. A topic map captures the subjects of which resources speak, and the relationships between subjects, in a way that is implementation-independent.

Variations of the Illustrated Embodiments

It is understood that the above-described arrangements are only illustrative of the application of the basic principles of the present invention. Numerous modifications and alternative arrangements may be devised by those skilled in the art without departing from the spirit and scope of the present invention. The appended claims are intended to cover such modifications and arrangements.

For example, it is noted that there is no requirement for the basic principal of the illustrated invention to be strictly related to medical technology. It is contemplated by the present invention to include other technologies and areas of research, such as: engineering, law, chemistry, physics, literature, accounting, business, and history. The prior lists are not exhaustive but merely illustrative of the wide birth of applications for the basic concepts of the present invention. The only criteria that is universally applied to the above listed items is a need to provide detailed and comprehensive material related to a specific area of knowledge that is, at least partially, based on image recognition and assessing certain issues for an appropriate course of action.

Therefore, as outlined above, the general form of the presently illustrated invention should not be limited to the field of medical publishing and diagnosis, wherein there is described: a unique method and system for allowing easy access to reference information regarding diagnosis, image capture and medical education, such as: clinical/pathological differential diagnosis details with links to specific diagnosis information, key facts, clinical presentation, pathology features, imaging findings, related images, such as clinical photos, drawings, etc., related anatomy information, references with abstracts, links to case information, such as index cases, common cases and uncommon cases, case information, expert imaging center information, such as providing critical protocols, validate procedures and research guidelines, CME, web service which will use the system's API to export data for other uses, content management both for content submission, content authoring tools and content approval, systems management for system usage and tracing analysis, branding/licensing management and system administration, and a host of other important materials.

Although as illustrated, for example, the screens, lists, buttons and images have certain shapes, sizes, and positions, each is contemplated to be variable with respect to all of those characteristics. Also, in one embodiment, the present invention utilizes the SNOMED lexicon as discussed above. In other embodiments, UMLS®, MeSH may be used.

It may be illustrated in each of the embodiments to use a particular type of central data repository, content management processes, product outputs, such as to PDA, and to system management; however, it is well within the capabilities of one skilled in the art to easily adapt the basics of the claimed features of the present invention into any other forms of content database management, product and digital media display means. For example, the diagnostic reference system contemplates not only Internet access, but intranet, personal computer CPU access, PACS access, tablet PC, wireless cell phones access as well other forms of access are clearly contemplated. The only limit is the necessity for providing a means for some data storage, processing and display mechanism and navigation means between successive screen displays. Therefore, this invention is not limited to any data storage device, like a server, nor is it limited to any communication device, such as the Internet, nor is it limited to any display device, such as a computer monitor, but is intended to offer an electronic clinical reference and education system and navigation means for a complex assembly of information that is related to, and has function with, text, imagery or figures.

Furthermore, as long as the ontology is created in a sufficiently expressive model, it may be possible to use formal logic systems to prove the ontology to be internally consistent. The practical implication of this is that automated tools may be created to help human editors find and correct erroneous information, which ordinarily would be nearly impossible in a body of knowledge of the ultimate size and complexity of the invention's content database. Thus, it is contemplated that the invention will eventually interface at a semantic level with other knowledge repositories.

Furthermore, it is anticipated that the Invention may function fully and independently without having to utilize any topic maps, ontologies, lexicon, semantic layers or thesaurus features. It is anticipated that the use of other technologies (e.g., Java and XML) may well obviate the need for use of any or all of these other technologies or applications.

The invention claimed is:

1. In a computer system including a computer having a processor and memory, a method of creating a clinical reference material on a desired topic, the method comprising:
   receiving a hierarchy of medical data from an author using an electronic authoring tool comprising a user interface including:
      a) a master outline authoring tool, which is used by the author to create the hierarchy of medical data,
      b) a diagnostic authoring tool, which is used by the author to create the diagnosis information; and
      c) a case authoring tool, which is used by the author to enter and edit the plurality of images and text,
   wherein the hierarchy of medical data includes:
      a plurality of diagnoses;
      a plurality of anatomical regions;
      a plurality of pathologies; and
      relational data describing relationships between the diagnoses, anatomical regions, and pathologies, each diagnosis defining at least one medical condition that is associated with at least one anatomical region and pathology;
   storing the hierarchy of medical data in a relational database in the memory of the computer, wherein the hierarchy of medical data is organized according to the relational data;
   receiving diagnosis information from the author for each of the plurality of diagnoses, wherein the diagnosis information describes general characteristics of each of the plurality of diagnoses;
   storing the diagnosis information of each of the plurality of diagnoses in the relational database with the corresponding diagnosis in the plurality of diagnoses;
   receiving a plurality of images and text relating to a particular case from the author, the images and text being associated with a particular diagnosis stored in the relational database;
   storing the plurality of images and text relating to the particular case in the relational database such that the images and text are associated with the particular diagnosis;
   receiving a first request from a user for medical reference data on a desired topic;
   retrieving the requested medical reference data from the relational database, wherein the medical reference data include at least some of the plurality of images and text, diagnosis information, and medical data related to the first request from the relational database stored in the memory of the computer;
   presenting the requested medical reference data to the user in a navigable user interface wherein the navigable user interface is presented on a display of a user computer according to the hierarchy of medical data;
   receiving a second request for clinical reference material from the user via the navigable user interface, wherein the clinical reference material includes a selected subset of the medical reference data in a requested format;
   reformatting the selected subset of the medical reference data received by the author into the requested format requested by the user to form the requested clinical reference material; and
   sending the requested clinical reference material to the user in the requested format.

2. The method of claim 1, further including the step of allowing the author or another entity to review the hierarchy of medical data prior to storing it in the relational database.

3. The method of claim 1, wherein the requested clinical reference material is a printed book.

4. The method of claim 1, wherein the requested clinical reference material is an electronic book.

5. The method of claim 1, wherein the medical data is created by the author using one or more graphical user interfaces.

6. The method of claim 1, wherein the diagnosis information is created by the author using one or more graphical user interfaces.

7. The method of claim 1, wherein plurality of images and text relating to a particular case is created by the author using one or more graphical user interfaces.

8. An electronic clinical reference and education system, comprising:
   an electronic authoring tool comprising a user interface including:
      a) a master outline authoring tool, which is used by the author to create the hierarchy of medical data,
      b) a diagnostic authoring tool, which is used by the author to create the diagnosis information; and
      c) a case authoring tool, which is used by the author to enter and edit the plurality of images and text,
   through which an author creates:
      a hierarchy of medical reference data including:
         a plurality of diagnoses;
         a plurality of anatomical regions;
         a plurality of pathologies; and
         relational data describing relationships between the diagnosis, anatomical regions, and pathologies, each diagnosis defining at least one medical condition that is associated with at least one anatomical region and pathology;
      diagnosis information for each of the plurality of diagnoses, wherein the diagnosis information describes general characteristics of each of the plurality of diagnoses;
      a plurality of images and text relating to a particular case from the author, the images and text being associated with a particular diagnosis stored in a relational database;
   the relational database which receives the hierarchy of medical reference data, diagnosis information, and plurality of images and text and storing the hierarchy of medical reference data, diagnosis information, and plurality of images and text in the relational database in a memory, wherein the diagnosis information and plurality of images and text are stored according to the hierarchy of medical reference data so that they are associated with the corresponding diagnosis in the hierarchy of medical reference data; and
   a diagnostic reference system including a processor connected to the relational database, which:
      retrieves and presents the medical reference data stored in the relational database in to a user connected to the reference system via a navigable user interface;

receives a request from the user for clinical reference material on a desired subset of the medical reference data in a requested format;

retrieves the requested medical reference data from the relational database;

reformats the selected subset of the medical reference data received by the author into the requested format in order to form the requested clinical reference material; and sends the requested clinical reference material to the user in the requested format.

9. The system of claim 8 wherein the diagnostic reference system comprises an expert imaging center protocol advisor for providing imaging protocols to imaging technician.

10. The system of claim 8, further comprising a continuing medical education system connected to the diagnostic reference system tracks the amount of time the user spends accessing medical reference data using the navigable user interface.

11. The system of claim 10, wherein the continuing medical education system also includes a testing module which tests the user knowledge of the medical reference data that the user has accessed, storing the results of the testing, and granting the user continuing medical education credits when the user has passed the testing.

12. The system of claim 8, wherein the relational database comprises a server connected to the Internet and wherein the electronic authoring tool and diagnostic reference system are connected to the relational database via the Internet.

13. An electronic clinical reference and education system including a computer having a processor and memory, the system comprising:

an electronic authoring tool comprising a user interface including:
 a) a master outline authoring tool, which is used by the author to create the hierarchy of medical data,
 b) a diagnostic authoring tool, which is used by the author to create the diagnosis information; and
 c) a case authoring tool, which is used by the author to enter and edit the plurality of images and text, through which an author creates:
 a hierarchy of medical reference data including:
  a plurality of diagnoses;
  a plurality of anatomical regions;
  a plurality of pathologies;
  and relational data describing relationships between the diagnosis, anatomical regions, and pathologies, each diagnosis defining at least one medical condition that is associated with at least one anatomical region and pathology;
 diagnosis information for each of the plurality of diagnoses, wherein the diagnosis information describes general characteristics of each of the plurality of diagnoses;
 a plurality of images and text relating to a particular case from the author, the images and text being associated with a particular diagnosis stored in a relational database;

the relational database including the memory which receives the hierarchy of reference data, diagnosis information, and plurality of images and text and stores the hierarchy of reference data, diagnosis information, and plurality of images and text in a relational database in the memory, wherein the diagnosis information and plurality of images and text are stored according to the hierarchy of reference data so that they are associated with the corresponding diagnosis in the hierarchy of reference data; and a product deployment process including the processor connected to the relational database, which:
 retrieves and presents the medical reference data stored in the relational database in to a user connected to the reference system via a navigable user interface;
 receives a request from the user for clinical reference material on a desired subset of the medical reference data in a requested format;
 retrieves the requested medical reference data from the relational database;
 reformats the selected subset of the medical reference data received by the author into the requested format in order to form the requested clinical reference material; and
 sends the requested clinical reference material to the user in the requested format;

a system management process tracking a user use of the product deployment process and analyzing the user use of the product deployment process.

14. The electronic clinical reference and education system of claim 13, wherein the product deployment process further performs an analysis of the plurality of reference content received from the plurality of authors in order to ensure the integrity and accuracy of the reference content.

15. The electronic clinical reference and education system of claim 14, wherein the analysis of the reference content further comprises sending the plurality of reference content received from the author to one or more editors for analysis.

16. The electronic clinical reference and education system of claim 13, wherein the product deployment process comprises a diagnostic reference system, whereby a user may request and receive reference data from the relational database on a desired topic in order to assist in a diagnosis.

17. The electronic clinical reference and education system of claim 13, wherein the product deployment process comprises an expert imaging center system, whereby a user may request and receive reference data from the relational database on a desired topic in order to identify an appropriate imaging protocols which may be used in a particular imaging process.

18. The electronic clinical reference and education system of claim 13, wherein the product deployment process comprises an continuing education system, whereby the user requests and is presented with educational reference data.

* * * * *

UNITED STATES PATENT AND TRADEMARK OFFICE
CERTIFICATE OF CORRECTION

PATENT NO. : 7,593,967 B2  Page 1 of 1
APPLICATION NO. : 10/723018
DATED : September 22, 2009
INVENTOR(S) : Harnsberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 739 days.

Signed and Sealed this

Twenty-eighth Day of September, 2010

David J. Kappos
*Director of the United States Patent and Trademark Office*